United States Patent
Snavely

(10) Patent No.: US 7,223,742 B2
(45) Date of Patent: May 29, 2007

(54) ENHANCED SOLUBILITY OF RECOMBINANT PROTEINS

(75) Inventor: Marshall Davenport Snavely, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 49 days.

(21) Appl. No.: 10/997,535

(22) Filed: Nov. 23, 2004

(65) Prior Publication Data

US 2005/0106681 A1    May 19, 2005

Related U.S. Application Data

(60) Continuation of application No. 09/507,166, filed on Feb. 18, 2000, now abandoned, which is a division of application No. 08/997,918, filed on Dec. 24, 1997, now Pat. No. 6,077,689.

(51) Int. Cl.
*A01N 43/04* (2006.01)

(52) U.S. Cl. ............ 514/44; 435/69.1; 435/69.7; 536/23.1; 536/23.4

(58) Field of Classification Search .......... None
See application file for complete search history.

(56) References Cited

U.S. PATENT DOCUMENTS

| | | | |
|---|---|---|---|
| 4,673,641 A | 6/1987 | George et al. | |
| 5,322,930 A | 6/1994 | Tarnowski et al. | |
| 5,597,719 A | 1/1997 | Freed et al. | |
| 5,623,054 A * | 4/1997 | Zhang et al. ............ | 530/370 |
| 5,629,172 A | 5/1997 | Mascarenhas et al. | |
| 5,654,176 A | 8/1997 | Smith | |

FOREIGN PATENT DOCUMENTS

| | | |
|---|---|---|
| EP | 0 207 044 A1 | 12/1986 |
| EP | 0 293 249 B1 | 11/1988 |
| WO | WO 92/13955 | 8/1992 |
| WO | WO 94/02502 | 2/1994 |
| WO | WO 94/23040 | 10/1994 |
| WO | WO 95/04076 | 2/1995 |
| WO | WO 95/16044 | 6/1995 |
| WO | WO 97/23614 | 7/1997 |

OTHER PUBLICATIONS

Aitken, *TIBS*, 20: 95-97 (1995).
Alam et al., *J. Biochem.*, 116: 416-425, (1994).
Argos, *J. Mol. Biol.*, 211: 943-958 (1990).
Ausubel et al., eds, *Current Protocols in Molecular Biology*, Greene Publishing Assoc. Inc. and John Wiley & Sons, Inc., NY (1994) (Table of Contents Provided).
Ausubel et al., eds, *Current Protocols in Molecular Biology*, Section 10.11.8, John Wiley & Sons, NY (1993).
Chames et al., *FEBS*, 405: 224-228 (1997).
Devlin et al., *J. Leukoc. Biol.*, 41: 302-306 (1987).
Engels et al., *Angew. Chem. Intl. Ed.*, 28: 716-734 (1989).
Falconer et al., *Biotechnol Bioeng*, 53: 453-458 (1997).
Flaschel et al., *Biotech Adv.*, 11: 31-78 (1993).
Genbank Database, Accession No. U09376.
Hattori et al., *PNAS*, 87: 5983-5987 (1990).
Jones et al., *Blood*, 76: 31-35 (1990).
Jones et al., *J. Mol. Biol.*, 245: 375-384 (1995).
Kane, *Curr. Opin. Biotechnol.*, 6: 494-500 (1995).
Lu et al., *Proc. Natl. Acad. Sci. USA*, 89: 11490-11494 (1992).
Lu et al., *The Plant Cell*, 6: 501-510 (1993).
Marais et al., *Curr. Biol.*, 3: 751-753 (1995).
Marston et al., *Meth. Enz.*, 182: 264-275 (1990).
Mottershead et al., *Journal of Cellular Biochemistry*, 61: 325-337 (1996).
Reuther et al., *Vitamins and Hormones*, 52: 149-175 (1996).
Rooney et al., *Plant Physiol.*, 107: 283-284 (1995).
Sambrook et al, *Molecular Cloning: A Laboratory Manual*, Cold Spring Harbor Laboratory Press, Cold Spring Harbor, NY (1989) (Table of Contents Provided).
Simonet et al., *Cell*, 89: 309-319 (1997).
Wang et al., *J. Mol. Evol.*, 43: 384-398 (1996).
Wu et al., *Plant Physiol.*, 114: 1421-1431 (1997).

* cited by examiner

*Primary Examiner*—Anish Gupta
(74) *Attorney, Agent, or Firm*—Marshall, Gerstein & Borun LLP

(57) ABSTRACT

Disclosed are methods for improving the solubility of a protein of interest produced recombinantly by expressing the protein of interest as a fusion protein with a member of the 14-3-3 family of proteins.

13 Claims, 9 Drawing Sheets

FIG. 1
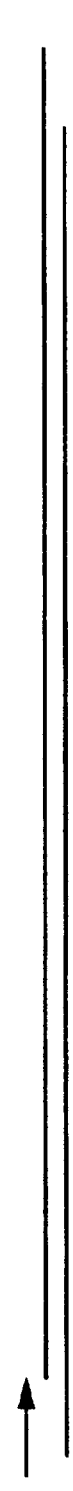
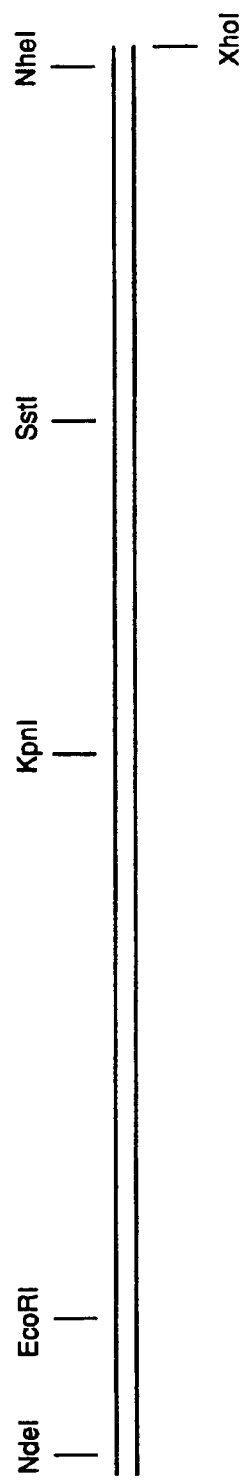
GF14 Sense strand oligos ("Set 1"):
GF14 Anti-sense Strand Oligos ("Set 2"):
Add 5' phosphate with polynucleotide kinase
Mix Set 1 and Set 2, boil, and anneal:
Add Dna ligase:
Add 5' oligos for Set 1 and Set 2 as PCR primers:
PCR product:
NdeI  EcoRI  KpnI  SstI  NheI  XhoI

FIG. 2

```
ATGGCTTCCGGCAGAGAAGAACTGGTTTACATGGCTAGACTGGCTGAACAGGC
TGAACGTTACGAAGAAATGGTTGAATTCATGGAAAAAGTTTCCGCTGCTGTTG
ACGGTGACGAACTGACCGTTGAAGAACGTAACCTGCTGTCCGTTGCTTACAAA
AACGTTATCGGTGCTCGTCGTGCTTCCTGGCGTATCATCTCCTCCATCGAACA
GAAAGAAGAATCCCGTGGTAACGACGACCACGTTACCGCTATCCGTGAATACC
GTTCCAAAATCGAAACCGAACTGTCCGGTATCTGCGACGGTATCCTGAAACTG
CTGGACTCCCGTCTGATCCCGGCTGCTGCTTCCGGTGACTCCAAAGTTTTCTA
CCTGAAAATGAAAGGTGACTACCACCGGTACCTGGCTGAGTTTAAAACCGGTC
AGGAACGTAAAGACGCTGCTGAACACACCCTGGCTGCTTACAAATCCGCTCAG
GACATCGCTAACGCTGAACTGGCTCCGACCCACCCGATCCGTCTGGGTCTGGC
TCTGAACTTCTCCGTTTTCTACTACGAAATCCTGAACTCCCCGGACCGTGCTT
GCAACCTGGCTAAACAGGCTTTCGACGAAGCTATCGCTGAGCTCGACACCCTG
GGTGAAGAATCCTACAAAGACTCCACCCTGATCATGCAGCTGCTGCGTGACAA
CCTGACCCTGTGGACCTCCGACATGCAGGACGACGCTGCTGACGAAATCAAAG
AAGCTGCTGCTCCGAAACCGACCGAAGAACAGCAGGCTAGCTAA
```

FIG. 7

ATGGAAACTTTTCCACCTAAATATCTTCATTATGATGAAGAAACTAGTCACCAGC

TGCTGTGCGACAAATGTCCTCCGGGTACCTACCTGAAACAGCACTGCACCGCTAA

ATGGAAACCGTTTGCGCTCCTTGTCCGGACCACTACTACACCGACTCCTGGCAC

ACCTCCGACGAATGCCTGTACTGCTCACCGGTTTGCAAGGAGCTGCAGTACGTTA

AACAGGAATGCAACCGTACGCACAACCGTGTATGCGAATGCAAAGAAGGTCGTTA

CCTGGAGATCGAATTCTGCCTGAAACACCGTTCCTGTCCGCCTGGTTTCGGTGTT

GTACAGGCTGGTACCCCGGAACGTAACACCGTTTGCAAACGTTGCCCGGACGGTT

TCTTCTCCAACGAAACCTCGAGCAAAGCTCCGTGCCGTAAACACACCAACTGCTC

CGTTTTCGGTCTCCTGTTAACCCAGAAAGGTAACGCTACCCACGACAACATCTGC

TCCGGTAACTCCGAGTCGACCCAGAAATAA

SEQUENCE LISTING

```
<160> NUMBER OF SEQ ID NOS: 59

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
ctggtttaca tggctaaact ggctgaacag gctgaacgtt acga            44

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
agaaatggtt gaattcatgg aaaaagtttc cgctgctgtt gacgg           45

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
tgacgaactg accgttgaag aacgtaacct gctgtccgtt gctta           45

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
```

```
caaaaacgtt atcggtgctc gtcgtgcttc ctggcgtatc atctc            45
```

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5

```
ctccatcgaa cagaaagaag aatcccgtgg taacgacgac cacgt            45
```

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6

```
taccgctatc cgtgaatacc gttccaaaat cgaaaccgaa ctgtc            45
```

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7

```
cggtatctgc gacggtatcc tgaaactgct ggactcccgt ctgat            45
```

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8

```
cccggctgct gcttccggtg actccaaagt tttctacctg aaaat            45
```

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9

```
gaaaggtgac taccaccggt acctggctga gtttaaaacc ggtca            45
```

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10

```
ggaacgtaaa gacgctgctg aacacaccct ggctgcttac aaatc            45
```

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
cgctcaggac atcgctaacg ctgaactggc tccgacccac ccgat            45

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
ccgtctgggt ctggctctga acttctccgt tttctactac gaaat            45

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
cctgaactcc ccggaccgtg cttgcaacct ggctaaacag gcttt            45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
cgacgaagct atcgctgagc tcgacaccct gggtgaagaa tccta            45

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
caaagactcc accctgatca tgcagctgct gcgtgacaac ctgac            45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
cctgtggacc tccgacatgc aggacgacgc tgctgacgaa atcaa            45

```
<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
agaagctgct gctccgaaac cgaccgaaga acagcaggct agctaa                46

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
gtttcggagc agcagcttct tgatttcgt cagcagcgtc                        40

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
gtcctgcatg tcggaggtcc acagggtcag gttgtcacgc agcag                 45

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
ctgcatgatc agggtggagt ctttgtagga ttcttcaccc aggt                  45

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
gtcgagctca gcgatagctt cgtcgaaagc ctgtttagcc aggtt                 45

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
gcaagcacgg tccggggagt tcaggatttc gtagtagaaa acgga                 45
```

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
gaagttcaga gccagaccca gacggatcgg gtgggtcgga gccag        45

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
ttcagcgtta gcgatgtcct gagcggattt gtaagcagcc agggt        45

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
gtgttcagca gcgtctttac gttcctgacc ggttttaaac tcagc        45

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 26
caggtaccgg tggtagtcac ctttcatttt caggtagaaa acttt        45

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
ggagtcaccg gaagcagcag ccgggatcag acgggagtcc agcag        45

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
tttcaggata ccgtcgcaga taccggacag ttcggtttcg atttt        45

<210> SEQ ID NO 29

```
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
ggaacggtat tcacggatag cggtaacgtg gtcgtcgtta ccacg         45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
ggattcttct ttctgttcga tggaggagat gatacgccag gaagc         45

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
acgacgagca ccgataacgt ttttgtaagc aacggacagc aggtt         45

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 32
acgttcttca acggtcagtt cgtcaccgtc aacagcagcg gaaac         45

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 33
tttttccatg aattcaacca tttcttcgta acgttcagcc tgttc         45

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 34
agccagttta gccatgtaaa ccagttcttc acgaccggaa gccat         45

<210> SEQ ID NO 35
<211> LENGTH: 39
```

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 35
cacaccacag atcccatat ggcttctggt cgtgaagaa                              39

<210> SEQ ID NO 36
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 36
caacacccac tcgagttagc tagcctgctg ttcttcggtg c                          41

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 37
ccacacccag ctagcctgct gttcttcggt cggtttcgga gcagcagc                   48

<210> SEQ ID NO 38
<211> LENGTH: 786
<212> TYPE: DNA
<213> ORGANISM: Artificial Sequence
<220> FEATURE:
<223> OTHER INFORMATION: Description of Artificial Sequence: Full length
      synthetic GF-14R gene

<400> SEQUENCE: 38
atggcttccg gcagagaaga actggtttac atggctagac tggctgaaca ggctgaacgt      60
tacgaagaaa tggttgaatt catggaaaaa gtttccgctg ctgttgacgg tgacgaactg     120
accgttgaag aacgtaacct gctgtccgtt gcttacaaaa acgttatcgg tgctcgtcgt     180
gcttcctggc gtatcatctc ctccatcgaa cagaaagaag aatcccgtgg taacgacgac     240
cacgttaccg ctatccgtga ataccgttcc aaaatcgaaa ccgaactgtc cggtatctgc     300
gacggtatcc tgaaactgct ggactcccgt ctgatcccgg ctgctgcttc cggtgactcc     360
aaagttttct acctgaaaat gaaaggtgac taccaccggt acctggctga gtttaaaacc     420
ggtcaggaac gtaaagacgc tgctgaacac accctggctg cttacaaatc cgctcaggac     480
atcgctaacg ctgaactggc tccgacccac ccgatccgtc tgggtctggc tctgaacttc     540
tccgttttct actacgaaat cctgaactcc ccggaccgtg cttgcaacct ggctaaacag     600
gctttcgacg aagctatcgc tgagctcgac accctgggtg aagaatccta caaagactcc     660
accctgatca tgcagctgct gcgtgacaac ctgaccctgt ggacctccga catgcaggac     720
gacgctgctg acgaaatcaa agaagctgct gctccgaaac cgaccgaaga acagcaggct     780
agctaa                                                               786

<210> SEQ ID NO 39
<211> LENGTH: 39
<212> TYPE: DNA
```

<213> ORGANISM: Artificial Sequence
<220> FEATURE:
<223> OTHER INFORMATION: Description of Artificial Sequence:
      Oligonucleotide

<400> SEQUENCE: 39
cacccaaccg ctagcggtac tggcgacccc aagttcgag                39

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40
cacccaaccg gatccattag tccaggtcgc tag                33

<210> SEQ ID NO 41
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 41
cacccagcta gcaataacga tgacgatgac aaaactccat taggtcctgc                50

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 42
cacccactcg agattacggc tgagccagat g                31

<210> SEQ ID NO 43
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 43
cacccagcta gcaataacga tgacgatgac aaagcaccgt actggacc                48

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 44
cacaccacac tcgagattat tccaggtagt ccgg                34

<210> SEQ ID NO 45
<211> LENGTH: 51
<212> TYPE: DNA
<213> ORGANISM: Artificial Sequence -continued

```
<220> FEATURE:
<223> OTHER INFORMATION: Description of Artificial Sequence:
      Oligonucleotide

<400> SEQUENCE: 45
cacaccacaa ggatccccaa taccgacgat gacaaagcac cgtactggac c         51

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 46
cacaccacac tcgagattat tccaggtagt ccgg                             34

<210> SEQ ID NO 47
<211> LENGTH: 525
<212> TYPE: DNA
<213> ORGANISM: Artificial Sequence
<220> FEATURE:
<223> OTHER INFORMATION: Description of Artificial Sequence: Synthetic
      DNA fragment encoding amino acids 22-194 of human OPG

<400> SEQUENCE: 47
atggaaactt ttccacctaa atatcttcat tatgatgaag aaactagtca ccagctgctg    60
tgcgacaaat gtcctccggg tacctacctg aaacagcact gcaccgctaa atggaaaacc   120
gtttgcgctc cttgtccgga ccactactac accgactcct ggcacacctc cgacgaatgc   180
ctgtactgct caccggtttg caaggagctg cagtacgtta acaggaatg caaccgtacg    240 cacaaccgtg tatgcgaatg caaagaaggt cgttacctgg agatcgaatt ctgcctgaaa   300
caccgttcct gtccgcctgg tttcggtgtt gtacaggctg gtaccccgga acgtaacacc   360
gtttgcaaac gttgcccgga cggtttcttc tccaacgaaa cctcgagcaa agctccgtgc   420
cgtaaacaca ccaactgctc cgttttcggt ctcctgttaa cccagaaagg taacgctacc   480
cacgacaaca tctgctccgg taactccgag tcgacccaga aataa                  525

<210> SEQ ID NO 48
<211> LENGTH: 55
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 48
caccaaaccg ctagcaataa cgatgacgat gacaaagaaa cttttccacc taaat         55

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 49
cacaacacag gatccattat ttctggg                                      27

<210> SEQ ID NO 50
<211> LENGTH: 50
```

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 50
cacccagtcg acccagaaag gttctacttc cggtgcttcc ggtcgtgaag            50

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 51
cacccaggat ccattactgc tgttcttcgg                                  30

<210> SEQ ID NO 52
<211> LENGTH: 10
<212> TYPE: PRT
<213> ORGANISM: Artificial Sequence
<220> FEATURE:
<221> NAME/KEY: PEPTIDE
<222> LOCATION: (4)
<223> OTHER INFORMATION: Amino acid sequence of the 14-3-3 polypeptide
      (where Xaa = Leu or Ile)
<220> FEATURE:
<223> OTHER INFORMATION: Description of Artificial Sequence: Internal
      14-3-3 polypeptide fragment

<400> SEQUENCE: 52

Arg Asn Leu Xaa Ser Val Ala Tyr Lys Asn
 1               5                  10

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Internal
      14-3-3 polypeptide fragment

<400> SEQUENCE: 53

Ala Ser Asn Asn Asp Asp Asp Asp Lys
 1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Internal
      14-3-3 polypeptide fragment

<400> SEQUENCE: 54

Arg Leu Gly Leu Ala Asn
 1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence:
      Enterokinase cut site
```

```
<400> SEQUENCE: 55

Ser Thr Leu Ile Met Gln Leu Leu
 1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Peptidase
      cut site

<400> SEQUENCE: 56

Asp Asp Asp Asp Lys
 1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Peptidase
      cut site

<400> SEQUENCE: 57

Ala Ser Gly Thr Gly
 1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Peptidase
      cut site

<400> SEQUENCE: 58

Gly Ser Thr Ser Gly
 1               5

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Amino Acid
      Linker

<400> SEQUENCE: 59

Ile Glu Gly Arg Gly Ile Pro Asn Thr Asp Asp Asp Lys
 1               5                  10
```

ENHANCED SOLUBILITY OF RECOMBINANT PROTEINS

This application is a continuation of U.S. Ser. No. 09/507,166, filed Feb. 18, 2000, now abandoned which is a divisional of U.S. Ser. No. 08/997,918, filed Dec. 24, 1997, now U.S. Pat. No. 6,077,689 which are hereby incorporated by reference.

BACKGROUND

1. Field of the Invention

This invention relates to methods of increasing the solubility of proteins produced recombinantly. Specifically, the invention is directed to production of recombinant proteins as fusion proteins in order to increase their solubility.

2. Related Art

1. Recombinant Protein Production

A variety of proteins of commercial value are now manufactured using recombinant DNA technology in which the DNA encoding the protein of interest is expressed in a host cell and then purified from that host cell. However, in some cases, this technology is not without problems. A number of heterologous proteins tend to aggregate in the host cell cytoplasm or periplasm when expressed recombinantly at high levels, thereby forming insoluble protein aggregate complexes commonly referred to as "inclusion bodies". When this occurs, the inclusion bodies are first isolated from the host cell, and the protein aggregate is then solubilized.

2. Fusion Proteins

One method that has been developed to enhance the solubility of recombinantly produced proteins of interest (and, in some cases, to simplify their purification from the host cell) is to prepare the protein of interest as a "fusion protein". To prepare a fusion protein (also known as a "chimeric protein"), the gene encoding the protein of interest can be attached to a second gene encoding a second protein, termed a "fusion partner". In this way, a single polypeptide is produced by the host cell, and the polypeptide is comprised of the protein of interest and the fusion partner.

The fusion partner may be homologous (i.e., from the same species and/or strain as the host cell) or heterologous (i.e., from a species and/or strain other than that of the host cell) to the host cell. Examples of commonly used fusion partners include, inter alia, maltose binding protein ("MBP"), glutathione-s-transferase ("GST"), hexaHistidine ("hexaHis") the lacZ and trpE gene products, ubiquitin, and thioredoxin. While each of these fusion partners has been demonstrated to enhance the solubility of at least one protein of interest, certain other proteins of interest do not demonstrate enhanced solubility when linked to these fusion proteins.

In certain cases, particularly where it is desirable to obtain the protein of interest in a purified form, the fusion partner and protein of interest must be separated from each other after synthesis as a single polypeptide. One means to achieve this is to provide a peptide linker between the fusion partners. This is accomplished by adding a nucleic acid molecule encoding the peptide between the gene encoding the protein of interest and the gene encoding the fusion partner. Typically, this "linker sequence" DNA encodes an oligopeptide that is a "cleavage recognition sequence" for an endopeptidase such as enterokinase, Factor Xa, or thrombin. The endopeptidase, when presented with a fusion protein containing its specific linker sequence, can thus cleave the fusion protein into its two components.

For further discussions of fusion proteins see, for example, WO 95/04076, published 9 Feb. 1995; U.S. Pat. No. 5,629,172 issued 13 May 1997; WO 94/23040, published 13 Oct. 1994; Flaschel et al., Biotech Adv., 11:31–78 (1993); European patent application 207,044, published 30 Dec. 1986; U.S. Pat. No. 5,322,930, issued 21 Jun. 1994; European Patent 293,249, published 30 Nov. 1988; U.S. Pat. No. 5,654,176, issued 5 Aug. 1997; WO 95/16044, published 15 Jun. 1995; WO 94/02502, published 3 Feb. 1994; and WO 92/13955, published 20 Aug. 1992.

3. 14-3-3 Proteins

The 14-3-3 family of proteins are acidic, highly conserved proteins with numerous isoforms. Members of this family have been found in a variety of tissues from mammals, yeast, invertebrates, and plants. The biological functions of 14-3-3 proteins are diverse, but generally appear to involve protein-protein interactions, suggesting they may generally be considered to be modulators of activity of other proteins (for reviews of this family of proteins, see Marais et al. *Curr. Biol.*, 3:751–753 [1995]; Aiken, TIBS, 20:95–97 [1995]; Reutheret et al., *Vitamins and Hormones*, 52:149–175 [1996]; Wang et al., *J. Mol. Evol.*, 43:384–398 [1996]; U.S. Pat. No. 5,597,719, issued 28 Jan. 1997).

The GF-14 proteins from *Arabidopsis thaliana* are members of the 14-3-3 family of proteins. Several GF-14 genes have been cloned and sequenced (Wu et al. *Plant Physiol.*, 114:1421–1431 [1997]). One of these genes, GF-14 omega, has been shown to be expressed in *E. coli* as a dimer (Lu et al., *The Plant Cell*, 6:501–510 [1993]).

In view of the need to prepare recombinant proteins of pharmaceutical and agricultural importance in a cost-effective manner, there is a need in the art to provide novel methods of enhancing the solubility of these proteins, thereby eliminating the necessity of costly and time-consuming refolding procedures.

Accordingly, it is an object of the present invention to provide new methods of enhancing the solubility of recombinant proteins produced in bacterial host cells.

This and other such objectives will be readily apparent to the skilled artisan from this disclosure.

SUMMARY OF THE INVENTION

In one embodiment, the present invention provides a method of increasing the solubility of a protein of interest produced in a host cell comprising expressing the protein as a fusion protein with a 14-3-3 protein. Optionally, the protein of interest is selected from the group consisting of: extracellular domains of membrane-bound receptor proteins, cytokines and cytokine-like proteins, neurotrophins, and metalloproteases. Additionally, the host cell may be a prokaryotic cell such as a bacterial cell, and the bacterial cell may be an *E. coli* cell.

In another embodiment, the invention provides a method of increasing the solubility of a protein of interest produced in a host cell comprising expressing the protein as a fusion protein with a GF-14 polypeptide. Optionally, the GF-14 polypeptide may be GF-14R.

In yet another embodiment, the invention provides a method of increasing the solubility of a protein of interest produced in a host cell comprising expressing the protein as a fusion protein with a GF-14 polypeptide, wherein the fusion protein contains a linker peptide.

In still another embodiment, the invention provides GF-14 nucleic acid molecules such as GF-14R as set forth in SEQ ID NO: 38.

BRIEF DESCRIPTION OF THE DRAWINGS

FIG. 1 is a diagram of the strategy used to prepare a synthetic full length GF-14 gene. The strategy is described in detail in Example 1. Standard abbreviations are used for restriction enzymes.

FIG. 2 (SEQ ID NO: 38) depicts the sequence of a full length synthetic GF-14R gene. The nucleotide sequence, which is 786 bases in length, is based on the *Arabidopsis thaliana* DNA sequence, but incorporates some codon changes to optimize the sequence for *E. coli* expression. In addition, this sequence has a nucleotide change at base number 39, and two additional codons (encoding ala and ser) at the 3' end prior to the stop codon, which provide the terminal Nhe I restriction site. This GF-14R sequence codes for a protein that is different from the "wild type" GF14 polypeptide at amino acid number 13. Arginine is present at that position instead of the "wild type" lysine.

Lanes 6–9 are lysates from a culture of cells expressing the GF14R-EPOR fusion protein. Lane 6 is cell lysate from cultured cells prior to induction; Lane 7 is cell lysate from a culture induced with IPTG for about 3 hours; Lane 8 is insoluble protein from the induced cell culture; Lane 9 is soluble protein from the induced cell culture.

Figure 5:
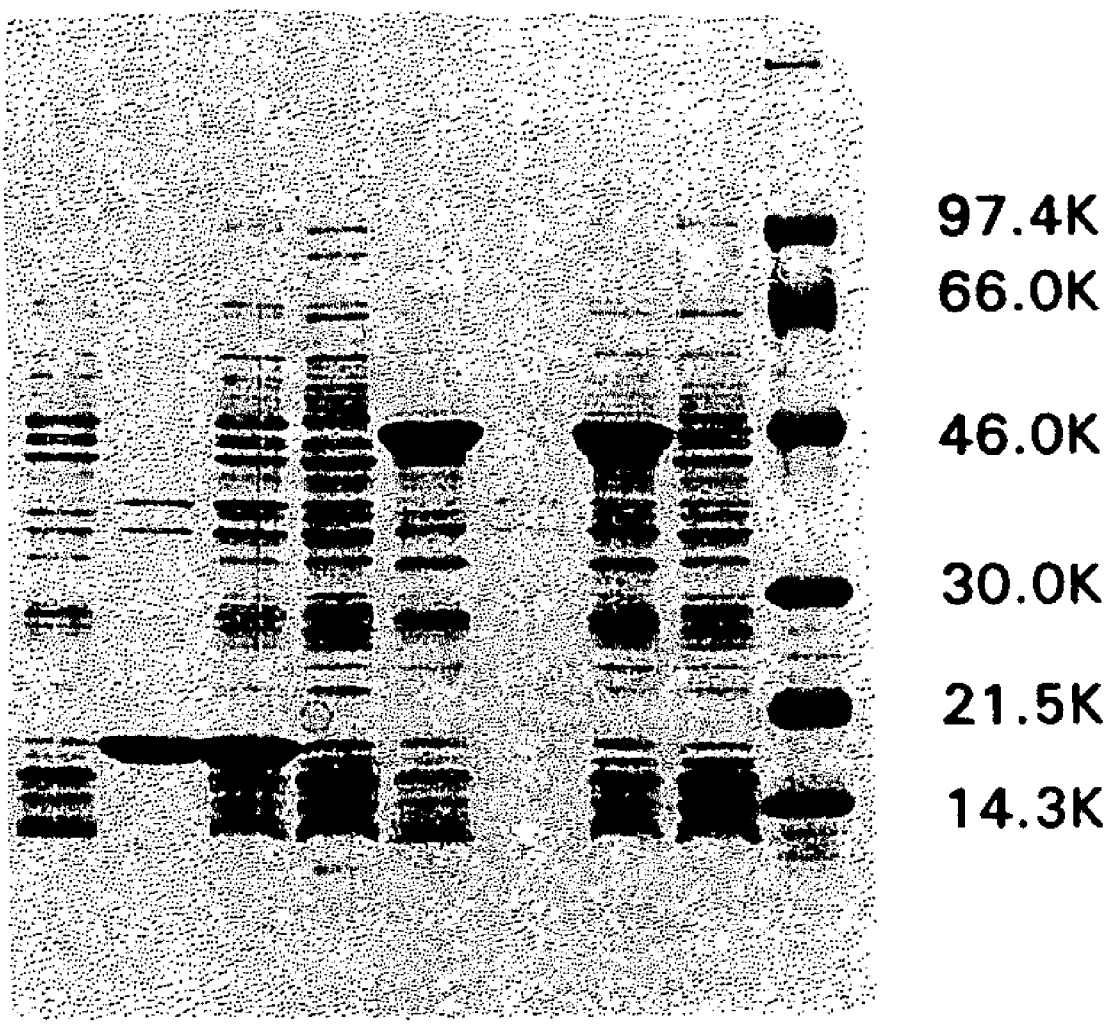

FIG. 5 depicts a SDS polyacrylamide gel used to visualize human GCSF protein expressed alone or as a fusion construct with GF-14R. The fusion protein was expressed in *E. coli* host cells. The 4–20 percent gel is stained with Coomassie blue. Lanes 1–4: lysates from a culture of cells containing pAMG22 GCSF; Lane 1 contains soluble fraction of the induced cell lysate; Lane 2 contains insoluble fraction of the induced cell lysate; Lane 3 contains cell lysate from a cell culture induced with IPTG for about 3 hours; Lane 4 contains cell lysate from a cell culture prior to induction.

Lanes 5–8 are lysates from a culture of cells transformed with the pAMG22/GF14R-GCSF construct; Lane 5 contains soluble fraction of the induced cell lysate; Lane 6 contains a sample of the insoluble fraction of the induced cell culture lysate; Lane 7 contains cell lysate from a cell culture induced with IPTG for about 3 hours; Lane 8 contains cell lysate from a cell culture prior to induction. Lane 9 contains molecular size markers.

Figure 6A:
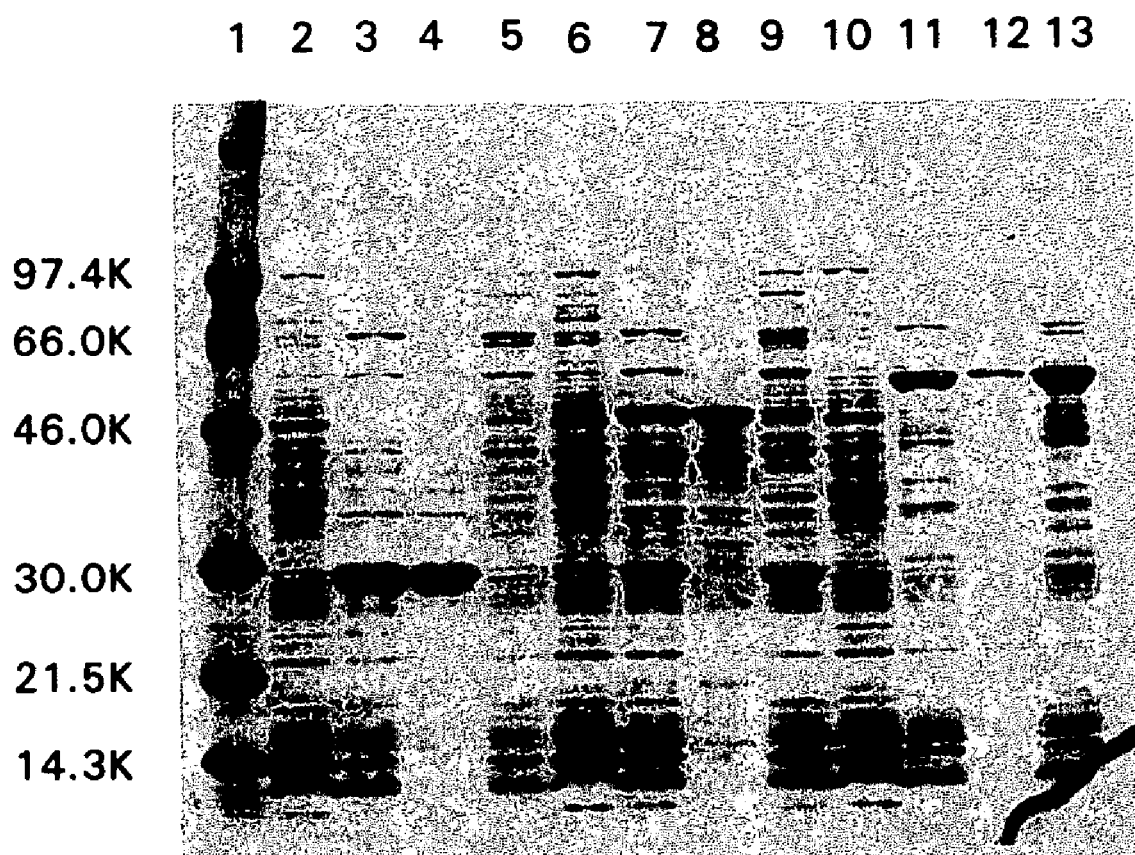
Figure 6B:
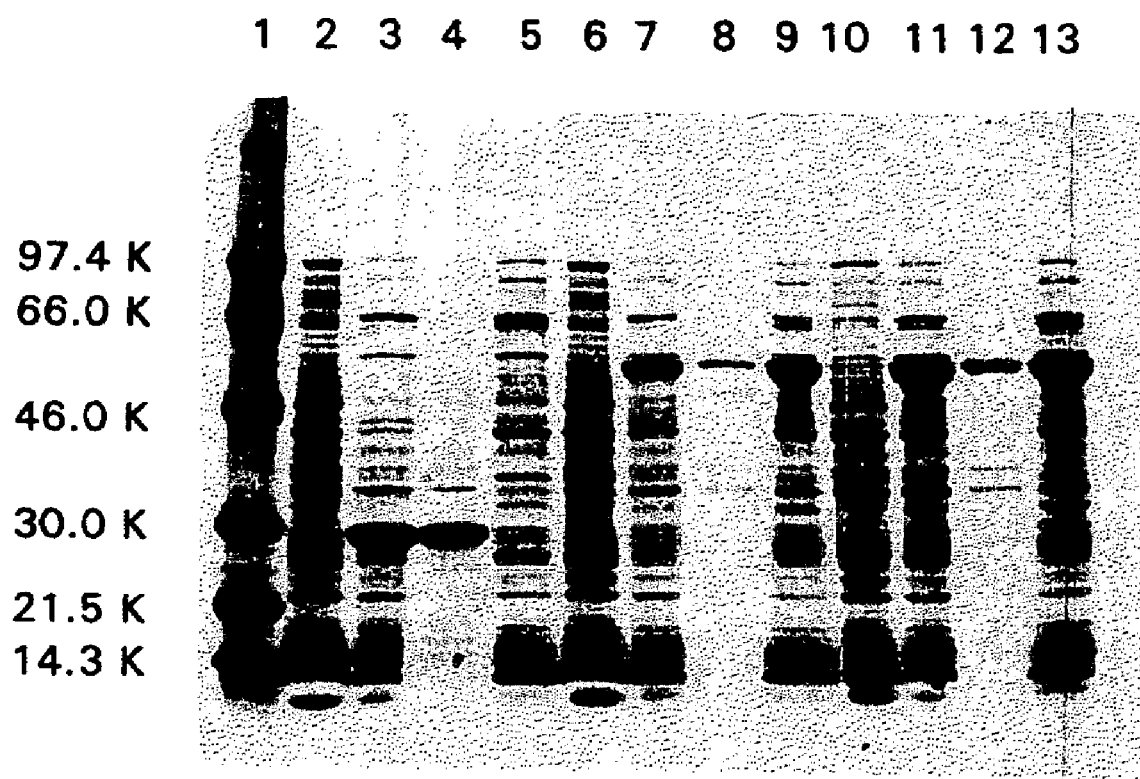

FIGS. 6A–6B depict SDS polyacrylamide gels stained with Coomassie blue. In FIG. 6A, Lane 1 contains molecular size markers.

In FIG. 6A, Lanes 2–5 are samples from cell cultures transformed with a DNA construct encoding the extracellular domain of human KGFR. Lane 2 is a sample of the cell lysate of a culture prior to induction; Lane 3 contains a sample of cell lysate from a culture induced with IPTG for about 3 hours; Lane 4 contains a sample of the insoluble fraction of the induced cell lysate; Lane 5 contains a sample of the soluble fraction of the induced cell lysate.

Lanes 6–9 of FIG. 6A depict samples from host cell cultures transformed with a DNA construct encoding, from 5' to 3', the GST protein and the extracellular domain of human KGFR. Lane 6 contains a sample of the cell lysate of a culture prior to induction; Lane 7 contains a sample of cell lysate from a culture induced with IPTG for about 3 hours; Lane 8 contains a sample of the insoluble fraction of cell lysate post-induction; Lane 9 contains a sample of the soluble fraction of the induced cell lysate.

Lanes 10–13 of FIG. 6A depict samples from host cell cultures transformed with a DNA construct encoding from 5' to 3', GF-14R and the extracellular domain of human KGFR. Lane 10 contains a sample of the host cell lysate of a culture prior to induction; Lane 11 contains a sample of cell lysate from a culture induced with IPTG for about 3 hours; Lane 12 contains a sample of the insoluble fraction of cell lysate post-induction; Lane 13 contains a sample of the soluble fraction of the induced cell lysate.

In FIG. 6B, Lanes 2–5 depict samples from a culture transformed with a DNA construct encoding the extracellular domain of the human KGFR. Lane 1 contains molecular size markers; Lane 2 contains cell lysate from a culture prior to induction; Lane 3 contains cell lysate from a culture induced with IPTG for about 3 hours; Lane 4 contains a sample of the insoluble fraction of the induced cell culture lysate; Lane 5 contains a sample of the soluble fraction of the induced cell culture lysate.

Lanes 6–9 of FIG. 6B contain samples from host cells transformed with a DNA construct comprising the extracellular domain of the human KGFR fused to the C-terminus of GF-14R. Lane 6 contains cell lysate from a culture prior to induction; Lane 7 contains cell lysate from a culture induced with IPTG for about 3 hours; Lane 8 contains a sample of the insoluble fraction of the induced cell culture lysate; Lane 9 contains a sample of the soluble fraction of the induced cell culture lysate.

Lanes 10–13 of FIG. 6B contain samples from host cells transformed with a DNA construct comprising the extracellular domain of the human KGFR fused to the C-terminus of GF-14. Lane 10 contains cell lysate from a culture prior to induction; Lane 11 contains cell lysate from a culture induced with IPTG for about 3 hours; Lane 12 contains a sample of the insoluble fraction of the induced cell culture lysate; Lane 13 contains a sample of the soluble fraction of the induced cell culture lysate.

FIG. 7 depicts the nucleotide sequence of a synthetic DNA fragment encoding human OPG22-194 (SEQ ID NO: 47). The sequence, which is 525 base pairs in length, has been optimized for expression in *E. coli*, and convenient restriction sites have been added in the coding region.

Figure 8:
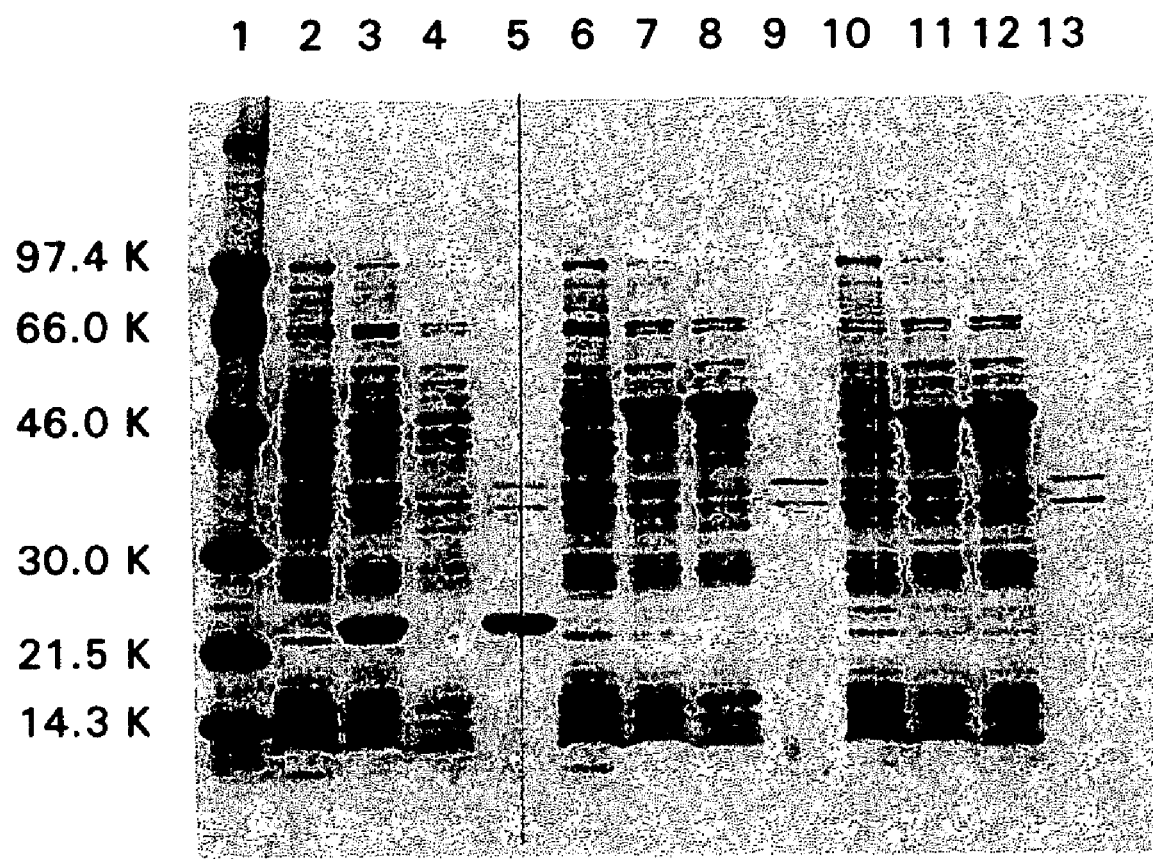

FIG. 8 depicts a SDS polyacrylamide gel used to visualize the truncated human OPG protein (amino acids 22–194) and two OPG22-194/GF-14R fusion protein constructs expressed in *E. coli* host cells. The 4–20 percent gel is stained with Coomassie blue. Lane 1 contains molecular size markers. Lanes 2–5 are samples of cell cultures in which the cells were transformed with a DNA construct containing the OPG fragment. Lane 2 is cell lysate from a culture prior to induction; Lane 3 is cell lysate from a culture induced with IPTG for about 3 hours; Lane 4 is soluble fraction of the induced cell lysate; Lane 5 is insoluble fraction of the induced cell lysate. Lanes 6–9 show samples from host cell cultures transformed with a construct comprising a portion of the human OPG gene fused at its 5' end to the GF-14R gene. Lane 6 contains cell lysate from a culture prior to induction; Lane 7 contains cell lysate from a culture induced with IPTG for about 3 hours; Lane 8 contains soluble fraction of the induced cell lysate; Lane 9 contains insoluble fraction of the induced cell lysate. Lanes 10–13 are samples from host cell cultures transformed with a construct comprising a portion of the human OPG gene fused at its 3' end to the GF-14R gene. Lane 10 contains cell lysate from a culture prior to induction; Lane 11 contains cell lysate from a culture induced with IPTG for about 3 hours; Lane 12 contains soluble fraction of the induced cell lysate; and Lane 13 contains insoluble fraction of the induced cell lysate.

DETAILED DESCRIPTION

This invention is based on the unexpected discovery that the solubility of a protein of interest, when expressed in a bacterial host cell, can be increased by expressing the protein as a fusion protein with a member of the 14-3-3 family.

The term "fusion protein" refers to two polypeptides or fragments of polypeptides (also called "fusion partners") which are synthesized in host cells from a nucleic acid molecule encoding both polypeptides (and optionally encoding a linker peptide as well) or fragments thereof. For purposes herein, one polypeptide of the fusion protein is a "14-3-3 polypeptide" or fragment thereof, and the other polypeptide is a "protein of interest" or fragment thereof. The fusion protein may have the 14-3-3 polypeptide situated at the amino terminus and the protein of interest situated at the carboxyl terminus, or vice versa. Optionally, the fusion protein may contain a "linker peptide" situated between the two fusion partners. The DNA construct encoding the fusion protein partners is referred to as the "fusion protein DNA" or the "fusion protein DNA construct".

The terms "protein of interest" and "polypeptide of interest" refer to a polypeptide produced recombinantly in a host cell as one member of a fusion protein. The polypeptide of interest may be homologous or heterologous to the host cell, and may be a naturally occurring polypeptide, or a substitution, deletion, and/or insertion variant of a naturally occurring polypeptide. Further, the polypeptide may be a full length molecule or a truncated version of the full length molecule. The polypeptide of interest may or may not have an amino terminal methionine. Optionally, the polypeptide of interest may itself be a fusion or chimeric polypeptide, such as, for example, where the Fc portion of an antibody is fused to the polypeptide of interest, where an affinity tag (such as hexaHis) is fused to the polypeptide of interest, and the like. Preferred polypeptides of interest include extracellular domains of receptor molecules, cytokines and cytokine-like molecules, neurotrophins, and metalloproteases.

The terms "14-3-3 polypeptides" and "14-3-3 polypeptide family" refer to those polypeptides having the following characteristics:

(1) the following 3 peptide sequences are present in the amino acid sequence of the 14-3-3 polypeptide (where N1=L or I):

```
RNL(N1)SVAYKN    (SEQ ID NO: 52)
RLGLAN           (SEQ ID NO: 53)
STLIMQLL         (SEQ ID NO: 54)
```

The 14-3-3 polypeptide will contain, from amino terminus to carboxyl terminus, SEQ ID NO: 52, SEQ ID NO: 53, and SEQ ID NO: 54. These three peptides may be found as a single contiguous sequence, but more likely will be separated by one or more amino acids;

(2) the full length polypeptide will have a net negative charge at pH 7.0; and (3) when expressed in a host cell as a fusion partner with a polypeptide of interest, the solubility of the polypeptide of interest is increased as compared with expression of the polypeptide of interest without the 14-3-3 fusion partner.

Included in this definition of 14-3-3 polypeptides are isoforms, as well as substitution, deletion, truncation, and/or insertion variants, whether natural or synthetic, of naturally occurring 14-3-3 polypeptides, as well as polypeptides encoded by nucleic acid molecules, wherein the nucleic acid molecule has been optimized for expression in prokaryotic host cells. Preferred 14-3-3 polypeptides include the GF-14 polypeptides from *Arabidopsis thaliana*, such as GF-14 omega, and human 14-3-3 proteins.

The term "GF-14 polypeptide" refers to those 14-3-3 polypeptides that naturally occur in *Arabidopsis thaliana*, and includes isoforms, as well as substitution, deletion, truncation, and/or any of the naturally occurring GF-14 polypeptides. Preferred GF-14 polypeptides include GF14 omega and GF-14R.

The term "linker peptide" refers to a peptide located between the two fusion partner polypeptides in a fusion protein construct. The linker peptide will generally consist of at least five to ten amino acids, but may optionally be longer. Typically, the amino acids will be chosen from the group of thr, ser, pro, asp, gly, lys, gin, asn, and ala, which are prevalent in naturally occurring linkers located between independently folding domains of proteins (see Argos, *J. Mol. Biol.* 211:943–958 [1990]). The amino acid sequence of the linker peptide may be a naturally occurring sequence or a synthetic sequence. Optionally, the linker peptide will have an endoproteinase site, such that the 14-3-3 portion of the fusion protein can be separated from the protein of interest after the fusion protein has been generated. Such endoproteinase sites include for example, the enterokinase cut site, asp-asp-asp-asp-lys (SEQ ID NO: 55). Preferred sequences for linker peptides are the enterokinase cut site, as well as the sequences: ala-ser-asn-asn-asp-asp-asp-asp-lys (SEQ ID NO: 56), ala-ser-gly-thr-gly (SEQ ID NO: 57), gly-ser-thr-ser-gly (SEQ ID NO: 58).

A DNA molecule encoding the full length protein of interest or fragment thereof can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds, (*Current Protocols in Molecular Biology*, Green Publishers Inc. and Wiley and Sons, NY [1994]). A gene or cDNA encoding the protein of interest or fragment thereof may be obtained for example by screening a genomic or cDNA library with a suitable probe. Suitable probes include, for example, oligonucleotides, cDNA fragments, or genomic DNA fragments, that are expected to have some homology to the gene encoding the protein of interest, such that the probe will hybridize with the gene encoding the protein of interest under selected hybridization conditions. An alternate means of screening a DNA library is by polymerase chain reaction "PCR" amplification of the gene encoding the protein of interest. PCR is typically accomplished using oligonucleotide "primers" which have a sequence that is believed to have sufficient homology to the gene to be amplified such that at least a sufficient portion of the primer will hybridize with the gene.

If the library to be screened is an expression library, an antibody which is believed to recognize and bind an epitope of the protein of interest can be used as a screening tool.

Alternatively, a gene encoding the protein of interest or fragment thereof may be prepared by chemical synthesis using methods well known to the skilled artisan such as those described by Engels et al. (*Angew. Chem. Intl. Ed.,* 28:716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the protein of interest will be several hundred nucleotides in length. Nucleic acids larger than about 100 nucleotides can be synthesized as several fragments using these methods. The fragments can then be ligated together to form the full length protein of interest. Usually, the DNA fragment encoding the amino terminus of the polypeptide will have an ATG, which encodes a methionine residue. This methionine may or may not be present on the mature form of the protein of interest, depending on whether the polypeptide produced in the host cell is secreted from that cell.

In some cases, it may be desirable to prepare nucleic acid and/or amino acid variants of the naturally occurring protein of interest. Nucleic acid variants (wherein one or more nucleotides are designed to differ from the wild-type or naturally-occurring protein of interest) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in bacterial host cells. Other preferred variants are those encoding conservative amino acid changes. (e.g., wherein the charge or polarity of the naturally occurring amino acid side chain is not altered substantially by substitution with a different amino acid) as compared to wild type.

A DNA molecule encoding a 14-3-3 polypeptide can be prepared using the methods described above for preparation of the gene encoding the protein of interest. Preferred variants of 14-3-3 polypeptides include GF14 omega and human 14-3-3 tau with the nucleic acid sequence altered to optimize expression in *E. coli* and to introduce convenient restriction sites. A general discussion of codon optimization for expression in *E. coli* is described in Kane (*Curr. Opin. Biotechnol.* 6:494–500 [1995]).

Once the genes encoding the protein of interest and the 14-3-3 polypeptide have been obtained, they may be modified using standard methods to create restriction endonuclease sites at the 5' and/or 3' ends. Creation of the restriction sites permits the genes to be properly inserted into amplification and/or expression vectors. Addition of restriction sites is typically accomplished using PCR, where one primer of each PCR reaction typically contains, inter alia, the nucleotide sequence of the desired restriction site.

There are several ways to prepare the DNA construct encoding the fusion protein which comprises the 14-3-3 gene, the gene encoding the protein of interest, and, optionally, a DNA molecule encoding a linker peptide which is located between the two genes.

In one procedure, the 14-3-3 gene and gene encoding the protein of interest (the "fusion partner genes") can be ligated together in either orientation (eg., 14-3-3 gene at the 5' or 3' end of the construct). Where a linker DNA molecule is to be included, it can first be ligated to one of the fusion partner genes, and that construct can then be ligated to the other fusion partner gene. Ligations are typically accomplished using DNA ligase enzyme in accordance with the manufacturer's instructions.

A separate procedure provides for first ligating one fusion partner gene into the selected vector, after which the other fusion partner gene can be ligated into the vector in a position that is either 3' or 5' to the first fusion partner gene. Where a linker DNA molecule is to be included, the linker DNA molecule may be ligated to either fusion partner gene either before or after that gene has been ligated into the vector.

The gene or cDNA encoding the protein of interest or fragment thereof can be inserted into an appropriate expression vector for expression in a host cell. The vector is selected to be functional in the particular host cell employed (i.e., the vector is compatible with the host cell machinery such that amplification and/or expression of the gene encoding the protein of interest can occur).

Typically, the vectors used in any of the host cells will contain a promoter (also referred to as a "5' flanking sequence") and other regulatory elements as well such as an enhancer(s), an origin of replication element, a transcriptional termination element, a ribosome binding site element, a polylinker region for inserting the nucleic acid encoding the polypeptide to be expressed, and a selectable marker element. Each of these elements is discussed below. Optionally, the vector may contain a "tag" DNA sequence, i.e., an oligonucleotide sequence located at either the 5' or 3' end of the fusion DNA construct. The tag DNA encodes a molecule such as hexaHis, c-myc, FLAG (Invitrogen, San Diego, Calif.) or another small immunogenic sequence. When placed in the proper reading frame, this tag will be expressed along with the fusion protein, and can serve as an affinity tag for purification of the fusion protein from the host cell. Optionally, the tag can subsequently be removed from the purified fusion protein by various means such as using a selected peptidase for example.

The promoter may be homologous (i.e., from the same species and/or strain as the host cell), heterologous (i.e., from a species other than the host cell species or strain), hybrid (i.e., a combination of promoters from more than one source), synthetic, or it may be the native protein of interest promoter. Further, the promoter may be a constitutive or an inducible promoter. As such, the source of the promoter may be any unicellular prokaryotic or eukaryotic organism, any vertebrate or invertebrate organism, or any plant, provided that the promoter is functional in, and can be activated by, the host cell machinery.

The promoters useful in the vectors of this invention may be obtained by any of several methods well known in the art. Typically, promoters useful herein will have been previously identified by mapping and/or by restriction endonuclease digestion and can thus be isolated from the proper tissue source using the appropriate restriction endonucleases. In some cases, the full nucleotide sequence of the promoter may be known. Here, the promoter may be synthesized using the methods described above for nucleic acid synthesis or cloning.

Where all or only a portion of the promoter sequence is known, the complete promoter may be obtained using PCR and/or by screening a genomic library with suitable oligonucleotide and/or 5' flanking sequence fragments from the same or another species.

Suitable promoters for practicing this invention are inducible promoters such as the lux promoter, the lac promoter, the arabinose promoter, the trp promoter, the tac promoter, the tna promoter, synthetic lambda promoters (from bacteriophage lambda), and the T5 or T7 promoters. Preferred promoters include the lux, lac and arabinose promoters.

The origin of replication element is typically a part of prokaryotic expression vectors whether purchased commercially or constructed by the user. In some cases, amplification of the vector to a certain copy number can be important for optimal expression of the protein or polypeptide of interest. In other cases, a constant copy number is preferred. In any case, a vector with an origin of replication that fulfills the requirements can be readily selected by the skilled artisan. If the vector of choice does not contain an origin of replication site, one may be chemically synthesized based on a known sequence, and ligated into the vector.

The transcription termination element is typically located 3' of the end of the fusion protein DNA construct, and serves to terminate transcription of the RNA message coding for the fusion polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

Expression vectors typically contain a gene coding for a selectable marker. This gene encodes a protein necessary for the survival and growth of a host cell grown in a selective culture medium. Typical selection marker genes encode proteins that (a) confer resistance to antibiotics or other toxins, e.g., ampicillin, tetracycline, chloramphenicol, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, the chloramphenicol resistance gene, and the tetracycline resistance gene.

The ribosome binding element, commonly called the Shine-Dalgarno sequence in prokaryotes, is necessary for the initiation of translation of mRNA. The element is typically located 3' to the promoter and 5' to the coding sequence of the fusion protein DNA construct. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

Each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting can be accomplished by first filling in "sticky ends" using an enzyme such as Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

Another method for constructing the vector is to conduct all ligations of the various elements simultaneously in one reaction mixture. Here, many nonsense or nonfunctional vectors may be generated due to improper ligation or insertion of the elements, however the functional vector may be identified by expression of the selectable marker. Proper sequence of the ligation product can be confirmed by digestion with restriction endonucleases or by DNA sequencing.

After the vector has been constructed and a fusion protein DNA construct has been inserted into the proper site of the vector, the completed vector may be inserted into a suitable host cell for fusion protein expression.

Host cells suitable for the present invention are bacterial cells. For example, the various strains of *E. coli* (e.g., HB101, JM109, DH5α, DH10, and MC1061) are well-known host cells for use in preparing recombinant polypeptides. The choice of bacterial strain is typically made so that the strain and the expression vector to be used are compatible. Various strains of *B. subtilis, Pseudomonas* spp., other *Bacillus* spp., *Streptomyces* spp., and the like may also be employed in practicing this invention in conjunction with appropriate expression vectors.

Insertion (also referred to as "transformation" or "transfection") of the vector into the selected host cell may be accomplished using such methods as calcium phosphate precipitation or electroporation. The method selected will in part be a function of the type of host cell to be used. These methods and other suitable methods are well known to the skilled artisan, and are set forth, for example, in Sambrook et al., supra.

The host cells containing the vector (i.e., transformed or transfected host cells) may be cultured using one or more standard media well known to the skilled artisan. The selected medium will typically contain all nutrients necessary for the growth and survival of the host cells. Suitable media for culturing *E. coli* cells are, for example, Luria broth ("LB"), YT broth, SOB, SOC, and/or Terrific Broth ("TB").

Typically, the antibiotic or other compound useful for selective growth of the transformed cells is added as a supplement to the medium. The compound to be used will be determined by the selectable marker element present on the plasmid with which the host cell was transformed. For example, where the selectable element confers kanamycin resistance, the compound added to the culture medium will be kanamycin.

Host cells with vectors containing fusion protein DNA constructs under the control of constitutive promoters are capable of continuous fusion protein production throughout the host cell culture period. However, host cells with vectors containing fusion protein DNA constructs under the control of inducible promoters generally do not produce significant amounts of fusion protein unless the promoter is "turned on" by exposing the host cells to the proper temperature (for temperature inducible promoters) or chemical compound(s). For example, where the fusion protein DNA construct is under the control of the lac promoter, the compound IPTG (isopropyl β-D-thiogalactopyranoside) is typically added to the host cell culture medium to induce high-level protein production.

The solubility of the fusion protein, or of the protein of interest after it has been cleaved from the GF-14 fusion partner, can be determined using standard methods known in the art. Typically, host cells are collected three to four hours after induction and the cells are lysed. Cell lysis may be accomplished using physical methods such as homogenization, sonication, French press, microfluidizer, or the like, or by using chemical methods such as treatment of the cells with EDTA and a detergent (see Falconer et al., *Biotechnol. Bioengin.* 53:453–458 [1997]). In some cases, it may be advantageous to use both chemical and physical means.

Separation of soluble and insoluble material is typically accomplished by centrifugation at around 18,000×G for about 20 minutes. After the soluble and insoluble materials have been separated, visualization of soluble and insoluble fusion protein can be readily accomplished using denaturing gel electrophoresis. With this technique, equivalent volumes of soluble and insoluble fractions are applied to the gel, and the amount of fusion protein (or protein of interest and/or 14-3-3 polypeptide if the two have been previously separated by cleavage; see below) can be detected by staining the gel or by Western blot, provided an antibody specific for the fusion protein, the protein of interest, or the 14-3-3 polypeptide (depending on which entity is being assessed), or other appropriate Western blot "detection tool" is available.

Purification of the fusion protein or the protein of interest (if the cleavage step has already been conducted) from solution can be accomplished using a variety of techniques. If the polypeptide has been synthesized such that it contains a tag such as Hexahistidine ("hexaHis") or other small peptide such as myc or FLAG, for example, at either its carboxyl or amino terminus, it may essentially be purified in a one-step process by passing the solution over an affinity column where the column matrix has a high affinity for the tag or for the polypeptide directly (i.e., an antibody specifically recognizing the protein of interest). For example, polyhistidine binds with great affinity and specificity to nickel, thus an affinity column containing nickel (such as the Qiagen nickel columns) can be used for purification of the protein of interest/hexaHis (see for example, Ausubel et al., eds., *Current Protocols in Molecular Biology*, Section 10.11.8, John Wiley & Sons, New York [1993]).

Where the fusion protein and/or the protein of interest has no tag and no antibodies are available, purification may be accomplished using standard methods such as those set forth below and in Marston et al. (*Meth. Enz.*, 182:264–275 [1990]). Such procedures include, without limitation, ion exchange chromatography, hydroxylapatite chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

The present invention is useful for enhancing direct expression of recombinantly produced polypeptides, as inclusion body formation is decreased or prevented, and solubility of the polypeptide of interest is increased.

In some cases, the polypeptide of interest may not be biologically active when expressed as a fusion protein with a 14-3-3 polypeptide. One reason for this may be lack of folding or improper folding of the polypeptide by the host cell machinery. To enhance the proper folding of the polypeptide of interest, the host cells expressing the fusion construct containing the polypeptide of interest may also be transformed with individual chaperone proteins and/or groups of chaperone proteins that are known to facilitate proper folding. The novelty of this approach is that fusion to a 14-3-3 protein prevents inclusion body formation, allowing the molecular chaperones more time in which to interact with a slowly-folding, rapidly-produced, aggregation-prone protein of interest. Here, the fusion protein containing the polypeptide of interest will be co-expressed with one or more chaperone proteins, leading to enhanced folding and increased biological activity of the protein of interest.

Examples of chaperone proteins that may be suitable for this use include, without limitation, members of the HSP 70 (heat shock protein 70) family and their cohorts such as the DNAK and DNAJ proteins (which are native to *E. coli*), members of the HSP 60 family of proteins and their cohorts such as GROEL and GROES proteins (also native to *E. coli*), and members of the family of small heat shock proteins such as the protein SEC-1 from *C. elegans*.

Deposits

The following materials have been deposited with the American Type Culture Collection, 12301 Parklawn Drive, Rockville, Md. 20852: *E. coli* GM221 cells on Jan. 7, 1998 as accession number 202077.

The following Examples are intended for illustration purposes only, and should not be construed to limit the invention in any way.

EXAMPLES

Example 1

Preparation of GF-14 and GF-14R DNA

The DNA and amino acid sequences of the omega isoform of GF-14 (referred to herein simply as GF-14) from *Arabidopsis thaliana* are known (see Lu et al., *Proc. Natl. Acad. Sci. USA*, 89:11490–11494 [1992]). These sequences have been deposited in Genbank as accession number U09376, however there is a discrepancy in amino acid number 8 between the published sequence and the deposited sequence. The former lists this amino acid as phenylalanine, while the later lists it as leucine. In the work described herein, a leucine was used at amino acid position number 8.

GF-14 DNA was prepared based on the *Arabidopsis* sequence with the codons optimized for expression in *E. coli*. In addition, several nucleotides were altered to create convenient restriction sites within the coding region. The codon changes did not result in amino acid sequence changes.

The strategy for preparing the synthetic GF-14 gene may be best understood by referring to the diagram in FIG. 1. The restriction site additions are indicated in the Figure.

Seventeen oligonucleotides of about 45 bases each were synthesized using the phosphoramidite method for oligonucleotide synthesis. These oligonucleotides, when aligned 5' to 3', correspond to the nearly full length sense strand of *Arabidopsis* GF-14 DNA (except for 18 bases at the 5' end of the gene), with codon changes to optimize for *E. coli* expression. These 17 oligonucleotides are collectively referred to herein as "Set 1". The sequence of each of the 17 oligonucleotides of Set 1 is set forth below:

```
                            Set 1
CTGGTTTACATGGCTAAACTGGCTGAACAGGCTGAACGTTACGA
(SEQ ID NO:1)

AGAAATGGTTGAATTCATGGAAAAAGTTTCCGCTGCTGTTGACGG
(SEQ ID NO:2)

TGACGAACTGACCGTTGAAGAACGTAACCTGCTGTCCGTTGCTTA
(SEQ ID NO:3)

CAAAAACGTTATCGGTGCTCGTCGTGCTTCCTGGCGTATCATCTC
(SEQ ID NO:4)

CTCCATCGAACAGAAAGAAGAATCCCGTGGTAACGACGACCACGT
(SEQ ID NO:5)

TACCGCTATCCGTGAATACCGTTCCAAAATCGAAACCGAACTGTC
(SEQ ID NO:6)

CGGTATCTGCGACGGTATCCTGAAACTGCTGGACTCCCGTCTGAT
(SEQ ID NO:7)

CCCGGCTGCTGCTTCCGGTGACTCCAAAGTTTTCTACCTGAAAAT
(SEQ ID NO:8)
```

-continued
Set 1

GAAAGGTGACTACCACCGGTACCTGGCTGAGTTTAAAACCGGTCA
(SEQ ID NO:9)

GGAACGTAAAGACGCTGCTGAACACACCCTGGCTGCTTACAAATC
(SEQ ID NO:10)

CGCTCAGGACATCGCTAACGCTGAACTGGCTCCGACCCACCCGAT
(SEQ ID NO:11)

CCGTCTGGGTCTGGCTCTGAACTTCTCCGTTTTCTACTACGAAAT
(SEQ ID NO:12)

CCTGAACTCCCCGGACCGTGCTTGCAACCTGGCTAAACAGGCTTT
(SEQ ID NO:13)

CGACGAAGCTATCGCTGAGCTCGACACCCTGGGTGAAGAATCCTA
(SEQ ID NO:14)

CAAAGACTCCACCCTGATCATGCAGCTGCTGCGTGACAACCTGAC
(SEQ ID NO:15)

CCTGTGGACCTCCGACATGCAGGACGACGCTGCTGACGAAATCAA
(SEQ ID NO:16)

AGAAGCTGCTGCTCCGAAACCGACCGAAGAACAGCAGGCTAGCTAA
(SEQ ID NO:17)

Separately, seventeen different oligonucleotides were prepared; these seventeen oligonucleotides of about 45 bases each, when aligned 5' to 3', correspond to the nearly full length (except for 17 bases at the 5' end) anti-sense strand of the synthetic GF-14 gene. Codon changes were made to optimize for *E. coli* expression. These 17 oligonucleotides are collectively referred to herein as "Set 2". The sequence of each of these 17 oligonucleotides is set forth below:

Set 2

GTTTCGGAGCAGCAGCTTCTTTGATTTCGTCAGCAGCGTC
(SEQ ID NO:18)

GTCCTGCATGTCGGAGGTCCACAGGGTCAGGTTGTCACGCAGCAG
(SEQ ID NO:19)

CTGCATGATCAGGGTGGAGTCTTTGTAGGATTCTTCACCCAGGGT
(SEQ ID NO:20)

GTCGAGCTCAGCGATAGCTTCGTCGAAAGCCTGTTTAGCCAGGTT
(SEQ ID NO:21)

GCAAGCACGGTCCGGGGAGTTCAGGATTTCGTAGTAGAAAACGGA
(SEQ ID NO:22)

-continued
Set 2

GAAGTTCAGAGCCAGACCCAGACGGATCGGGTGGGTCGGAGCCAG
(SEQ ID NO:23)

TTCAGCGTTAGCGATGTCCTGAGCGGATTTGTAAGCAGCCAGGGT
(SEQ ID NO:24)

GTGTTCAGCAGCGTCTTTACGTTCCTGACCGGTTTTAAACTCAGC
(SEQ ID NO:25)

CAGGTACCGGTGGTAGTCACCTTTCATTTTCAGGTAGAAAACTTT
(SEQ ID NO:26)

GGAGTCACCGGAAGCAGCAGCCGGGATCAGACGGGAGTCCAGCAG
(SEQ ID NO:27)

TTTCAGGATACCGTCGCAGATACCGGACAGTTCGGTTTCGATTTT
(SEQ ID NO:28)

GGAACGGTATTCACGGATAGCGGTAACGTGGTCGTCGTTACCACG
(SEQ ID NO:29)

GGATTCTTCTTTCTGTTCGATGGAGGAGATGATACGCCAGGAAGC
(SEQ ID NO:30)

ACGACGAGCACCGATAACGTTTTTGTAAGCAACGGACAGCAGGTT
(SEQ ID NO:31)

ACGTTCTTCAACGGTCAGTTCGTCACCGTCAACAGCAGCGGAAAC
(SEQ ID NO:32)

TTTTTCCATGAATTCAACCATTTCTTCGTAACGTTCAGCCTGTTC
(SEQ ID NO:33)

AGCCAGTTTAGCCATGTAAACCAGTTCTTCACGACCGGAAGCCAT
(SEQ ID NO:34)

To prepare double stranded GF-14 DNA, about 50 pmol of each oligonucleotide in Set 1 was placed into a small tube together with ligase buffer (Boehringer Mannheim, Indianapolis, Ind.) in a final volume of about 100 µl. About 20 U of polynucleotide kinase (Boehringer Mannheim) were added to each tube in order to phosphorylate the 5' ends of the oligonucleotides. This mixture was incubated at 37° C. for fifteen minutes. Separately, the same procedure was followed for the Set 2 oligonucleotides.

The two reactions were then mixed together and boiled for about 5 minutes to inactivate the kinase and to denature any secondary structure present in the oligonucleotides. The mixture was allowed to cool slowly to 37° C. temperature to anneal the complementary top and bottom strands of the GF-14 oligonucleotides to each other. About five units of T4 DNA ligase (Boehringer Mannheim) were then added to the mixture and the reaction was incubated at about 16° C. for about 45 minutes to create a continuous double-stranded DNA molecule comprising one sense strand and one anti-sense strand, which contained most of the coding region for GF-14.

To generate full length double-stranded GF-14 DNA containing 5' sequence at both ends, the polymerase chain reaction (PCR) technique was used. The sense primer (SEQ ID NO:35) for PCR contained, from 5' to 3', a Bam HI restriction site, a Nde I restriction site, and 18 bases of 5' sense sequence of the GF-14 gene. The anti-sense PCR primer (SEQ ID NO:36) contained, from 5' to 3' (in the anti-sense strand direction), an Xho I restriction site, a stop codon, a Nhe I restriction site, and the 5' 17 bases of the anti-sense sequence of the GF-14 gene (with one error which caused an insertion near the 3' end of the coding region, see below). The Nhe I restriction site DNA sequence adds two amino acids, ser and ala, to the carboxy terminus of the GF-14 polypeptide.

SEQ ID NO:35
CACACCACAGGATCCCATATGGCTTCTGGTCGTGAAGAA

SEQ ID NO:36
CAACACCCACTCGAGTTAGCTAGCCTGCTGTTCTTCGGTGC

Forty cycles of PCR were conducted using the double stranded GF14 DNA as a template under the following parameters: 94° C. for 30 seconds; 37° C. for 30 seconds; and 72° C. for one minute. About five units of Amplitaq DNA polymerase (Perkin Elmer) were used with PCR buffer and nucleotide mixture from Boehringer Mannnheim in a final volume of about 100 µl. After PCR, a small aliquot of reaction product was run on an agarose gel to confirm that the PCR product generated was the correct size. The remaining PCR product was purified using QIAquick™ (Qiagen Corp., Chatsworth, Calif.) following the manufacturer's instructions.

The purified product was digested first with Bam HI and Xho I following the manufacturer's protocol (Boehringer Mannheim). The DNA was visualized on a 1 percent agarose gel stained with ethidium bromide. A band of about 800 bp was cut out of the gel and purified using Qiaex II® resin (Qiagen, Chatsworth, Calif.), following the manufacturer's protocol. The purified fragment was ligated into the vector pBluescript SK+® (Stratagene, La Jolla, Calif.) previously cut with the same enzymes using the same protocol, and purified the same way, except that the vector was treated with about 1 unit of calf intestinal phosphatase for 30 minutes at about 37° C. following digestion to prevent recircularization during ligation. The ligation was conducted in a volume of about 30 µl containing 2 mM ATP, 2 U of T4 DNA ligase (Boehringer Mannheim), about 30 ng of vector, 5–10 ng of insert, and ligase buffer (Boehringer Mannheim). The reaction was incubated overnight at about 16° C., ethanol precipitated, resuspended in 5 µl of water, and used to transform about 50 µl of competent E. coli cells by electroporation with a BioRad GenePulser (BioRad Laboratories, Hercules, Calif.) using 2.5 V, 25 µFD, and 200 ohms, and a cuvette with a gap length of about 2 mm.

After electroporation, the cells were allowed to recover in about 5 ml of Luria broth for about one hour at 30° C., after which the entire transformation mix was plated on Luria broth agar containing about 100 µg/ml ampicillin. Colonies were screened for the GF-14 clone by PCR using two oligonucleotides described above (SEQ ID NOS:35 and 36) for the sense and anti-sense strands. Colonies were picked directly into a PCR reaction mix containing 4 pmol of each primer, 0.2 mM DNTP, 1 U Taq polymerase, and PCR buffer (Boehringer Mannheim) in a final volume of about 20 µl. The PCR cycle parameters used were: 94° C. for 30 seconds, 37° C. for 30 seconds, 72° C. for one minute, with a total of 40 cycles. The PCR products were evaluated by agarose gel electrophoresis as described above.

Five clones yielding a fragment of the expected size (about 820 bp) were selected for DNA sequencing. Plasmid DNA was prepared using the Qiaprep® spin miniprep kit (Qiagen). Automated DNA sequencing identified some errors in the nucleotide sequences of several of these PCR clones. Three clones were selected, each of which contained regions of nearly correct sequence between restriction sites. Full length GF-14 DNA with a nearly correct nucleotide sequence was assembled from three fragments of these clones digested as follows: Nde I-Eco RI, Eco RI-Kpn I, and Kpn I-Xho I. The approximate positions of these restriction sites, relative to the full length GF-14 DNA are shown in FIG. 1.

The fragments were cloned into the vector pAMG22 (described in PCT WO 97/23614, published 3 Jul. 1997), behind the PS4 promoter, using standard ligation methods. Ligation products were transformed into E. coli GM221 host cells by electroporation as described above. Plasmid DNA was prepared as described above and the sequence of the GF-14 insert in the vector was verified by automated DNA sequencing. Four incorrect bases were identified in this clone as follows. Position 650 was "G" but should have been "A"; and position 653 was "C" but should have been "G". Corrections to these two errors were made by site-directed mutagenesis using the Quikchange® kit (Stratagene, La Jolla, Calif.) following the manufacturer's instructions. The third error was a "C" incorrectly inserted at position 764 due to an error in one of the original oligonucleotides used for PCR of the full length GF14 gene (SEQ ID NO: 36) This was removed by PCR as follows. An EcoRI-Nhe I fragment of about 700 bp was generated by PCR using the sense strand oligonucleotide containing the Eco RI site (set forth above as SEQ ID NO: 2) as the 5' primer, and the following oligonucleotide coding for the 3' end of the gene.

(SEQ ID NO: 37)
CCACACCCAGCTAGCCTGCTGTTCTTCGGTCGGTTTCGGAGCAGCAGC

PCR reactions were performed as described above except that thirty cycles were conducted under the following parameters: 94° C., 20 seconds; 37° C., 30 seconds; 72° C., one minute. The product was purified using QIAquick™ (Qiagen) and digested with EcoRI and NheI (Boehringer Mannheim) following the manufacturer's instructions.

The fourth error was a "G" at nucleotide position 39 that should have been an "A". This mutation resulted in a conservative change at amino acid position 13; an arginine was present instead of the wild type lysine. The DNA construct containing this error was called "GF-14R", and was used for many of the expression and fusion studies as described below. The DNA sequence of GF-14R is set forth in FIG. 2 (SEQ ID NO: 38). This sequence differs from wild type GF-14 DNA in that it is optimized for expression in E. coli cells, and contains a "G" at base number 39.

The "G" at position 39 was changed to "A" by site-directed mutagenesis (as described above) to generate a DNA molecule encoding "wild type" GF14 but with codon changes as appropriate for optimal expression in E coli. This GF14 gene coded for lysine instead of arginine at amino acid position 13, and was used to confirm that alteration of amino acid 13 did not affect the solubility properties of the native GF14 protein (see FIG. 6).

Example 2

Expression of GF-14R Polypeptide

Successful expression of GF-14R polypeptide from the GF-14R DNA inserted into the pAMG22 vector requires an E. coli strain such as GM221, JM109 (Invitrogen, Carlsbad, Calif.), OR XL1-blue (Stratagene, La Jolla, Calif.) that harbors the lac I$^q$ repressor.

To express the GF-14R polypeptide, a 5 ml culture was prepared in Luria broth containing about 40 µg/ml kanamycin. The culture was incubated overnight in an air shaker at 30° C. About 20 µl of this overnight culture were then used to inoculate 50 ml of Luria broth containing about 40 µg/ml kanaycin in a 250 ml shaker flask. The cells were grown on the bench overnight. The following day, the cell culture was placed in a shaking incubator at 30° C. and grown to an optical density at 600 nm of about 0.6 (Spectrophotomer model no. DU640, Beckman Instruments, Fullerton Calif.), after which a pre-induction sample was taken and about 0.4 mM IPTG was added to induce GF-14R polypeptide production.

Figure 3:
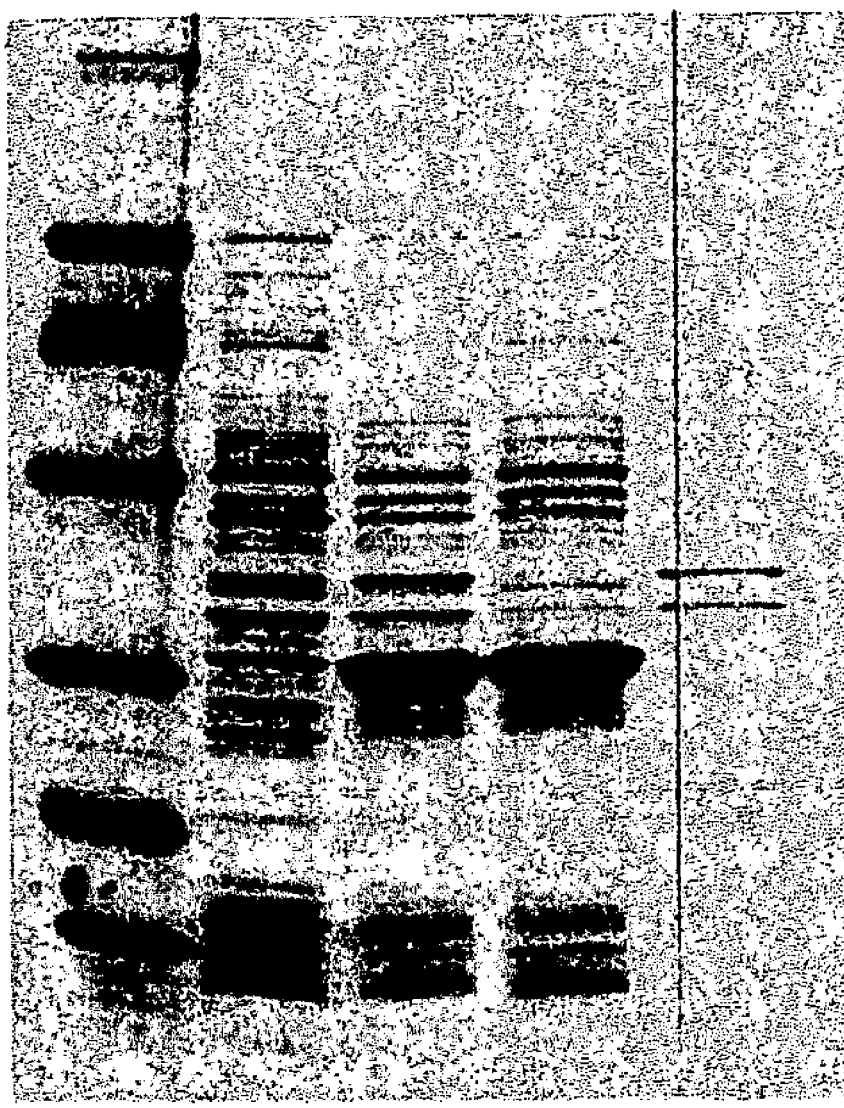
FIG. 3 is a copy of a SDS polyacrylamide gel used to visualize GF-14R protein (the DNA sequence of which is described in FIG. 2) expressed in *E. coli* host cells transformed with the DNA encoding GF-14R. The 16% gel is stained with Coomassie blue. Lane 1 is molecular size markers; Lane 2 is lysate from a cell culture prior to induction; Lane 3 is lysate from a cell culture induced with IPTG for about 3 hours; Lane 4 is a sample of the soluble fraction of the lysate from the induced cell culture; Lane 5 is a sample of the insoluble fraction of the cell lysate from the induced cell culture.

After about three to four hours shaking at 30° C., a post-induction sample was taken, the cells were pelleted, and resuspended in 10 ml of a buffer solution containing 10 mM Tris-HCl, pH 8.0 and 1 mM EDTA ("TE" buffer). The cells were then broken using a microfluidizer (M-110T, Microfluidics, Newton, Mass.) at an input pressure of about 85 psi and the solution was centrifuged at about 18,000×g for about 20 minutes to pellet insoluble material. After centrifugation, the supernatant was removed and the pellet was resuspended in an equal volume of TE. Equal amounts of supernatant and pellet fractions were analyzed by SDS-PAGE. This gel is shown in FIG. 3. As can be seen, a band of about 29 kDa was observed primarily in the soluble fraction. Therefore, it is apparent that GF-14R is predominantly soluble when expressed in E. coli.

The GF-14R mutant was expressed in E. coli GM221 host cells and was prepared and purified from a 1 liter culture in Luria broth containing about 40 μg/ml kanamycin. The culture was incubated on a shaker rotating at about 250 rpm, and cells were grown to an optical density at 600 nm of about 0.8 (as measured by a Beckman Model 35 Spectrophotomer). The culture was then induced by addition of about 4 ml of 100 mM IPTG. After about 3 hours, the cells were harvested by centrifugation, and stored as a frozen pellet at minus 80° C.

The cells were thawed, creating a cell paste which was resuspended in water and lysed in a microfluidizer (Microfluidics, Newton, Mass.). The cell debris was removed by centrifugation. A large majority of the GF-14R polypeptide was found in the soluble fraction. The supernatant was diluted two-fold with 20 mM Tris pH 8.0, and was then loaded onto a Sepharose Q Hitrap column (5 ml, Pharmacia, Piscataway, N.J.). The protein was eluted from the column using a salt gradient solution containing from 0 to 1 M sodium chloride in 20 mM Tris pH 8.0. The fractions containing GF-14R were identified by SDS PAGE and pooled. The pool was diluted about 20 fold with 10 mM sodium/potassium phosphate buffer pH 5.4, and then subjected to loading on to a second Q-Hitrap column (5 ml, Pharmacia). The GF-14R was eluted with a salt gradient from 0 to 0.5 M sodium chloride in 10 mM sodium potassium/phosphate buffer pH 5.4.

After the above chromatography steps, the GF-14R polypeptide was subjected to standard SDS-PAGE to further assess its purity. GF-14R was found to be highly pure by analysis of this Coomassie-stained gel. GF-14R migrated at about 30 kDa, which is consistent with a predicted molecular weight of about 29 kDa. To estimate its size, the protein was subjected to gel filtration using a Superose 12 column (1×30 cm; Pharmacia, Piscataway, N.J.) equilibrated with phosphate buffered saline ("PBS", Gibco-BRL, Grand Island, N.Y.) at room temperature with a flow rate of about 0.5 ml/minute. Molecular size analysis was conducted by light scattering as follows. The online light scattering/chromatography system used three detectors in series. The first of these was the Hewlett-Packard 1100 HPLC system (absorbance at 280 nm), followed by a Wyatt Mini-Dawn laser light scattering detector (Wyatt Inc., Santa Barbara, Calif.), and finally a Hewlett-Packard refractive detector (model no. HP 1047A).

Light scattering analysis indicated that the molecular weight of the GF-14R polypeptide is about 57 kDa, which is close to the 58 kDa predicted for a GF-14R homodimer. GF-14 expressed in E. coli has been reported to form a dimer (Lu et al., The Plant Cell, 6:501–510 [1994]; see also Alan et al., J. Biochem., 116:416–425, [1994]; Jones et al., J. Mol. Biol., 245:375–384, [1995], all of which demonstrate that other members of the 14-3-3 family of proteins form homodimers as well).

The conservative change at the N-terminus of GF-14R (lysine to arginine at amino acid position 13) and the addition of two amino acids, ser and ala (encoded by the Nhe I site), to the C-terminus of GF-14R did not affect homodimer formation.

Example 3

Preparation of Fusion Proteins
A. EPO Receptor

To prepare a DNA construct for expression of a GF-14R/erythropoietin receptor fusion protein ("GF-14R/EPOR"), the DNA encoding the extracellular domain of the human erythropoietin receptor ("EPOR") gene (Jones et al. Blood 76:31–35 [1990]), minus the signal sequence and the first seven amino acids of mature EPOR, was used as a template for PCR. The 5' primer for PCR contained, from 5' to 3', a NheI cut site, the DNA sequence encoding a linker molecule, and the coding sequence for the first five amino acids (beyond the seven amino acid deletion) for EPOR. The sequence of this oligonucleotide is set forth below:

(SEQ ID NO: 39)
CACCCAACCGCTAGCGGTACTGGCGACCCCAAGTTCGAG

The extracellular domain of EPOR contained the sequence from amino acid number 8 to amino acid number 225 of the mature polypeptide. The amino acid sequence of the linker polypeptide placed between the GF14R and EPOR was ala-ser-gly-thr-gly (SEQ ID NO:57). The 3' primer contained the complementary sequence of the last 14 bases of the gene coding for the EPOR extracellular domain, stop codon, and a Bam HI restriction site. The sequence of this oligonucleotide is set forth below:

CACCCAACCGGATCCATTAGTCCAGGTCGCTAG (SEQ ID NO: 40)

The PCR reaction solution contained about 2.5 units of Amplitaq DNA polymerase in a Perkin-Elmer buffer and nucleotide mixture. The final volume was about 100 μl. The conditions for this reaction were: 94° C. for 30 seconds, 37° C. for 30 seconds, and 72° C. for one minute. Thirty cycles of PCR were conducted. After PCR, a small amount of the PCR product was run on an agarose gel to confirm that a band of the proper size (about 700 bp) was obtained. The remainder of the PCR product was ethanol precipitated and then digested with Nhe I and Bam HI. This digested DNA was then ligated into the GF-14 expression vector (as prepared in Example I) previously cut with Nhe I and Bam HI.

E coli GM221 cells were transformed by electroporation with the EPOR/GF-14 DNA fusion construct using the electroporation method described in Example 1. The transformed cells were plated on Luria broth plates containing about 40 μg/ml of kanamycin. Colonies were screened by PCR using primers which hybridize to the vector sequence outside the cloned region. To prepare the plasmid DNA for PCR, colonies were picked directly into a reaction mix containing about 0.5 units of Amplitaq DNA polymerase (Perkin Elmer), together with buffer and nucleotides from the manufacturer in a final volume of 20 μl. The reaction conditions were: 94° C. for 20 seconds, 37° C. for 30 seconds, and 72° C. for 30 seconds, for a total of 30 cycles.

An aliquot from each PCR reaction was run on a 1 percent agarose gel. Two clones that had PCR products of the appropriate size (about 1800 bp) were selected. Plasmid DNA was isolated as described above, and was sequenced using standard automated sequencing methods to confirm that the sequence was correct.

Figure 4:
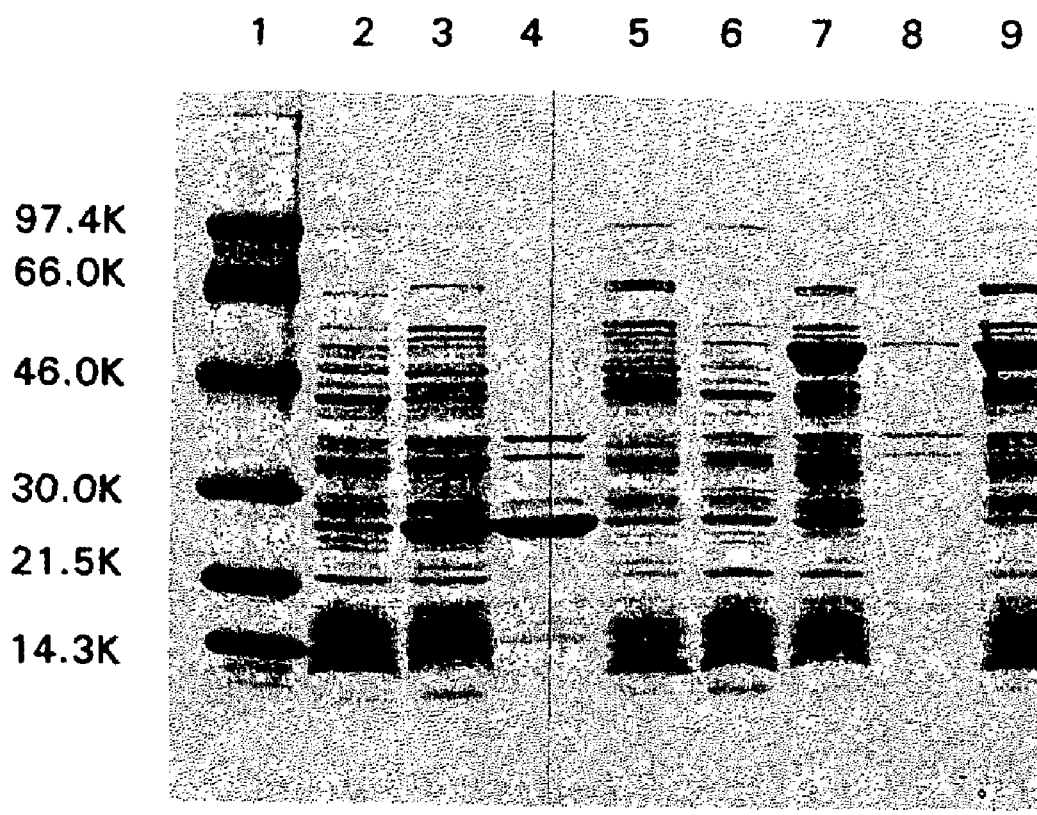
FIG. 4 depicts a SDS polyacrylamide gel used to visualize an extracellular domain of the human EPOR gene expressed alone or as a fusion construct with GF-14R in *E. coli* host cells. The gel is a 4-20 percent gel and is stained with Coomassie blue. Lane 1 is molecular size markers. Lanes 2–5 are lysates from a culture of cells expressing the EPOR gene fragment alone (i.e., without a fusion partner). Lane 2 is cell culture lysate prior to induction; Lane 3 is cell lysate from a cell culture induced with IPTG for about 3 hours; Lane 4 is an insoluble protein fraction of the induced cell culture lysate; Lane 5 is protein from the soluble fraction of the induced cell culture lysate.

To test expression and solubility of the fusion protein, an overnight culture of the selected clone in LB medium containing about 40 mg/ml kanamycin was used to inoculate a 50 ml culture of the same medium in a 125 ml shaken flask. Expression of the fusion protein was performed essentially as described in Example 1. Soluble and pellet fractions were prepared as described in Example 1 and analyzed by SDS-PAGE. This gel is shown in FIG. 4. As can be seen, EPOR when expressed alone, is largely insoluble (Lane 4; about 24 kDa). With the fusion construct, a band of the expected size of about 53 kDa was observed in both the soluble and pellet fractions (Lanes 8 and 9). However, the vast majority of the GF-14/EPOR fusion protein was found in the soluble fraction (Lane 9), suggesting that expression of the truncated EPOR gene as a fusion with GF-4R greatly enhances solubility.

B. GCSF Protein

The fusion of GCSF to GF-14 was accomplished in a manner similar to that described for the GF-14/EPOR fusion. A linker containing the nucleotide sequence encoding the enterokinase endopeptidase cut site was added to GCSF DNA (Devlin et al. *J. Leukoc. Biol.* 41:302–306 [1987]) by PCR as follows. The 5' oligonucleotide primer for this reaction was designed to contain a Nhe I restriction site, two asp codons, DNA encoding an enterokinase cut site, and the first 17 nucleotides of the 5' end of GCSF. The sequence of this oligonucleotide is set forth below:

```
                                            (SEQ ID NO: 41)
CACCCAGCTAGCAATAACGATGACGATGACAAAACTCCATTAGGTCCTGC
```

The 3' (antisense) oligonucleotide contained, from 5' to 3', an Xho I site, a stop codon, and the last 15 nucleotides of GCSF. The sequence of this oligonucleotide is set forth below:

```
CACCCACTCGAGATTACGGCTGAGCCAGATG   (SEQ ID NO: 42)
```

PCR was performed using conditions described above for construction of the GF14R/EPOR fusion construct. A DNA fragment of about 570 bp was generated. This PCR product was ethanol precipitated, and digested with Nhe I and Xho I. The resulting fragment was ligated into the GF-14 expression vector described in Example 1 which had been previously cut with the same enzymes and treated with calf intestinal phosphatase. The resulting vector contained, from 5' to 3' GF-14R DNA, a DNA fragment encoding two asp residues followed by an enterokinase cut site, and the gene encoding GCSF. The amino acid sequence of the polypeptide linker which contains an enterokinase cut site, is ala-ser-asn-asn-asp-asp-asp-asp-lys (SEQ ID NO: 56).

The vector containing the GF14R/GCSF fusion construct was transformed into *E. coli* GM221 cells according to the procedure described in Example 1. Several resulting clones were selected and subjected to PCR screening. Preparation of plasmid DNA from these clones was as described in Example 1, and automated DNA sequencing of the GCSF portion of the each insert was conducted to verify the sequence. A clone with the correct sequence was used for expression in *E. coli* cells as described in Example 1. The solubility of the GF-14R/GCSF fusion protein was examined by SDS-PAGE as described in Example 1. As can be seen in FIG. 5, GCSF expressed directly (i.e., without GF-14R) is almost entirely insoluble as evidenced by a prominent band of approximately 18 kDa in the insoluble fraction (Lane 2). However, the vast majority of the fusion protein (approximately 45 kDa) was found in the soluble fraction (Lane 5), indicating that the fusion protein is highly soluble.

C. KGF Receptor Protein

A fusion protein containing GF-14R and a portion of the human keritinocyte growth factor (KGFR) was prepared as follows. DNA encoding amino acids 64-289 of human KGFR, which contains immunoglobulin loops two and three of the extracellular domain of KGFR (see Hatteri et al. PNAS 87:5983–5987, [1990]) was obtained using standard cloning techniques. A Nhe I cut site and an enterokinase cut site were added to the 5' end of the KGFR DNA using PCR.

The 5' primer for PCR contained, from 5' to 3', an Nhe I cut site (which encodes amino acids ala and ser) two codons encoding asn, the enterokinase recognition site asp-asp-asp-asp-lys (SEQ ID NO: 55), and the first 15 bases of the KGFR gene as described above (i.e., starting at the codon for amino acid 64 of full length KGFR). The complete sequence of this primer is set forth below:

```
                                           (SEQ ID NO: 43)
CACCCAGCTAGCAATAACGATGACGATGACAAAGCACCGTACTGGACC
```

The 3' oligonucleotide for PCR contained, from 5' to 3', a XhoI restriction site, a stop codon, and 15 bases of the 3' end of the coding region for the KGFR extracellular domain. The sequence of this oligonucleotide is set forth below:

```
CACACCACACTCGAGATTATTCCAGGTAGTCCGG   (SEQ ID NO:44)
```

The PCR conditions for this reaction were: 94° C. for 30 seconds, 37° C. for 30 seconds, and 72° C. for one minute. Thirty cycles were performed using the KGFR DNA fragment described above as a template. The resulting PCR fragment was digested with NheI and XhoI and cloned into pAMG22 harboring GF-14R previously cut with the same enzymes and dephosphorylated. The cloning and sequence confirmation were performed as described in Example 1.

Polypeptide expression experiments were conducted as described in Example 1, and samples were run on a SDS polyacrylamide gel. The gel is shown in FIG. 6A. As can be seen, the KGFR protein (approximately 28 kDa; Lane 4) was insoluble when expressed as a single protein in *E. coli*. However, the GF14-KGFR fusion protein (approximately 57 kDa; Lane 13) was highly soluble when expressed in *E. coli*.

The same KGFR DNA fragment was also fused to a GF-14 DNA construct (i.e., the "arg" at amino acid position 13 was converted to the wild type "lys"). This construct was prepared as described in Example 1. Expression experiments were conducted as described above.

FIG. 6B shows that both GF-14 and GF-14R enhance solubility of the KGFR fragment to a similar extent.

D. KGFR-GST Fusion Protein

A Ba HI site and DNA coding for a six amino acid linker were added to the 5' end of the KGFR DNA fragment described above (i.e., the fragment encoding amino acids 64–289 of mature KGFR) by PCR using the following oligonucleotide.

CACACCACAAGGATCCCCAATACCGACGATGACAAAGCACCGTACTGGACC (SEQ ID NO:45)

This oligonucleotide also contained 15 bases of the 5' end of the KGFR DNA fragment.

The 3' oligonucleotide for PCR contained the 15 bases of the 3' end of the coding region for the KGFR fragment, a stop codon, and a XhoI site. The sequence of this 3' oligonucleotide is set forth below:

CACACCACACTCGAGATTATTCCAGGTAGTCCGG (SEQ ID NO:46)

The PCR reaction conditions were the same as those described above, and the same template was used. A DNA fragment of about 700 bp was generated and was digested with BamHI and XhoI. The digested fragment, which contained the coding sequence for amino acids 64-289 of KGFR, was cloned into the vector pGEX-5X-1 (Pharmacia, Piscataway, N.J.). This vector, which contains DNA coding for the protein GST, had been cut previously with Bam HI and Xho I and had been dephosphorylated.

Ligation of the KGFR fragment into the GST vector was carried out as described in Example 1. This ligation resulted in a GST-KGFR fusion construct in which the KGFR was fused to the C-terminus of GST. Cloning a fragment into pGEX-5X-1 at the Bam HI site adds a seven amino acid linker between the fusion partners. With the six amino acids that were added at the 5" end of the KGFR gene in the PCR reaction, the resulting amino acid linker between GST and the KGFR was thirteen amino acids and had the following sequence:

ile-glu-gly-arg-gly-ile-pro-asn-thr- (SEQ ID NO:59)
asp-asp-asp-lys

After transformation into *E. coli* GM221 cells using the electroporation procedure described in Example 1, plasmid DNA was prepared from selected colonies. Clones were identified as positive by digestion with restriction endonucleases. The region of the plasmid coding for the GST-KGFR fusion protein was analyzed by automated DNA sequencing.

Expression and solubility of the GST-KGFR fusion protein were analyzed as described in Example 1. A SDS gel of the expression results is shown in FIG. 6A. As is apparent, the majority of the GST/KGFR fusion protein was found in the insoluble fraction (approximately 52 kDa; Lane 8).

Based on these results, it is apparent that GF-14R and GF-14, when used as a fusion partners, enhance the solubility of proteins that remain insoluble when expressed with previously known fusion partners such as GST. Therefore, GF-14R, and the 14-3-3 class of polypeptides, provide a novel method for enhancing solubility of proteins that, under conventional techniques, are otherwise insoluble.

E. Osteoprotegerin Protein

A truncated version of the human osteoprotegerin gene, "OPG", containing amino acids 22-194 (Simonet et al. *Cell* 89:309–319 [1997]) is found in inclusion bodies (i.e., is insoluble) when expressed directly in *E. coli* cells. To evaluate the effect of GF-14 fusion with OPG on solubility of OPG, a fusion construct was prepared. In this construct, the DNA sequence was optimized for bacterial expression. The sequence of this synthetic OPG DNA fragment is set forth in FIG. 7.

To fuse OPG22-194 (which was modified for *E. coli* expression) to GF-14R, PCR was used to add a Nhe I site and a nine amino acid linker to the 5' end of the OPG coding region. The sequence of the amino acid linker between GF-14R and OPG, which contains an enterokinase cut site, is ala-ser-asn-asn-asp-asp-asp-asp-lys (SEQ ID NO: 56). The 5' oligonucleotide additionally contained 19 bases of the 5' end of the gene coding for OPG. The complete sequence of this oligonucleotide is set forth below:

CACCAAACCGCTAGCAATAACGATGACGATGACAAAGAAACTTTTCCACCTAAAT (SEQ ID NO:48)

The 3' oligonucleotide for this PCR reaction contained the terminal 3' 18 bases of the OPG22-194 DNA fragment, as well as a stop codon and a Bam HI site. The complete sequence of this oligonucleotide is set forth below:

CACAACACAGGATCCATTATTTCTGGG (SEQ ID NO:49)

The PCR reaction was performed as described in Example 3A using the OPG22-194 DNA fragment as a template. The size of the PCR product (about 570 bp) was checked by agarose gel electrophoresis. The remaining product was digested, after ethanol precipitation, with Nhe I and Bam HI. The resulting fragment was cloned into pAMG22 GF-14R cut with the same enzymes as described in Example 1, resulting in a fusion construct containing, from 5' to 3', GF-14R DNA, the linker sequence DNA, and the OPG DNA fragment. The DNA sequence coding for the GF14R OPG22-194 fusion protein was confirmed by automated DNA sequencing.

Expression experiments to generate a fusion protein in which GF-14R is at the amino end of the fusion and OPG is at the carboxyl end of the fusion protein were performed as described in Example 1, and samples of the expression experiments were run on a SDS gel. The results are shown in FIG. 8. As can be seen, nearly all of the OPG22-194 was insoluble when expressed alone (approximately 23 kDa; Lane 5), however, the vast majority of the fusion protein was found in the soluble fraction (approximately 49 kDa; Lane 8), indicating that expressing OPG as a fusion protein with GF-14R renders it soluble.

In a separate experiment, a fusion protein in which GF14R was fused to the C-terminus of OPG22-194 was generated. To accomplish this, a Sal I restriction site located close to the 3' end of the OPG22-194 construct was used. Cleavage at this restriction site removes DNA coding for the last three amino acids of the OPG22-194 sequence.

A 5' oligonucleotide was used for PCR that added a Sal I site, the final three amino acids of OPG22-194, and a five amino acid linker to the 5' end of the coding region of GF-14R. The amino acid sequence added by this oligonucleotide between OPG and GF14R was gly-ser-thr-ser-gly (SEQ ID NO: 58). The 5' oligonucleotide for the PCR reaction also contained 17 bases matching the 5' end of the GF14R gene. The sequence of this oligonucleotide is set forth below:

CACCCAGTCGACCCAGAAAGGTTCTACTTCCGGTGCTTCCGGTCGTGAAG(SEQ ID NO:50)

The 3' oligonucleotide for this PCR reaction contained 14 bases of DNA coding for GF14R, a stop codon and a BamHI site. The sequence of this oligonucleotide is set forth below:

CACCCAGGATCCATTACTGCTGTTCTTCGG    (SEQ ID NO:51)

A PCR reaction was performed with these oligonucleotides as described in Example 3A using the vector pAMG22 containing GF-14R as template, and the size of the expected product (about 830 bp) was confirmed by agarose gel electrophoresis using a small aliquot of the reaction mixture. The remainder of the PCR product was precipitated with ethanol and digested with Sal I and Bam HI. The resulting fragment was cloned into pAMG21 containing OPG22-194 (see PCT WO 97/23614, published 3 Jul. 1997 for a description of pAMG21), digested with the same restriction enzymes and transformed into E. coli GM221 cells as described in Example 1. Plasmid DNA was prepared using methods described above, and the DNA sequence of the region obtained from PCR was verified by automated DNA sequencing. Expression experiments, performed as described in Example 1, demonstrated that the majority of the fusion protein (approximately 47 kDa; Lane 12) was found in the soluble fraction. This result indicates that GF14R can enhance solubility when fused to either the amino or carboxy terminus of the fusion partner. Therefore, the relative positions of GF14R and the fusion partners do not affect the solubility of the chimeric protein.

I claim:

1. An isolated and purified nucleic acid molecule comprising the sequence as set forth in SEQ ID NO: 38.

2. An isolated nucleic acid molecule encoding a fusion protein comprising a 14-3-3 polypeptide and a protein of interest, wherein the nucleic acid sequence comprises SEQ ID NO:38.

3. The nucleic acid molecule according to claim 2 wherein the coding region for the 14-3-3 polypeptide is located 5' to the coding region for the protein of interest.

4. The nucleic acid molecule according to claim 2 wherein the protein of interest is selected from the group consisting of an extracellular domain of a membrane-bound receptor protein, a cytokine or cytokine-like protein, a neurotrophin and a metalloprotease.

5. The nucleic acid molecule according to claim 2 wherein the encoded fusion protein further comprises a linker peptide located between the 14-3-3 polypeptide and the protein of interest.

6. The nucleic acid molecule according to claim 5 wherein the linker peptide comprises between five and ten amino acids.

7. The nucleic acid molecule according to claim 5 wherein the linker peptide comprises amino acids selected from the group consisting of threonine, serine, proline, aspartate, glycine, lysine, glutamine, asparagine and alanine.

8. The nucleic acid molecule according to claim 5 wherein the linker peptide further comprises an endopeptidase recognition site.

9. The nucleic acid molecule according to claim 5 wherein the linker peptide comprises a sequence selected from the group consisting of SEQ ID NOS: 55–58.

10. A vector comprising the isolated nucleic acid molecule according to claim 2.

11. A host cell comprising the vector according to claim 10.

12. A method of making a nucleic acid molecule encoding a fusion protein comprising a 14-3-3 polypeptide and a protein of interest, the method comprising the steps of:
   (a) obtaining a first nucleic acid encoding a protein of interest; and
   (b) joining the first nucleic acid to the isolated nucleic acid according to claim 2, thereby making a nucleic acid molecule encoding the fusion protein.

13. The method according to claim 12 further comprising joining a third nucleic acid encoding a linker peptide between the first nucleic acid and the isolated nucleic acid according to claim 2.

* * * * *

UNITED STATES PATENT AND TRADEMARK OFFICE
CERTIFICATE OF CORRECTION

PATENT NO. : 7,223,742 B2 Page 1 of 1
APPLICATION NO. : 10/997535
DATED : May 29, 2007
INVENTOR(S) : Marshall Davenport Snavely It is certified that error appears in the above-identified patent and that said Letters Patent is hereby corrected as shown below:

Column 6, Line 29, replace "gin" with --gln--.

Column 12, Line 4, replace "Parkiawn" with --Parklawn--.

Column 15, Line 52, replace "DNTP," with --dNTP,--.

Column 19, Line 20, replace "GF-4R" with --GF-14R--.

Column 20, Line 63, replace "Ba HI site" with --BamHI site--.

Signed and Sealed this

Twenty-ninth Day of April, 2008

JON W. DUDAS
*Director of the United States Patent and Trademark Office*